US012133695B2

(12) United States Patent
Laviola et al.

(10) Patent No.: US 12,133,695 B2
(45) Date of Patent: *Nov. 5, 2024

(54) ULTRASOUND LOCALIZATION SYSTEM WITH ADVANCED BIOPSY SITE MARKERS

(71) Applicant: HOLOGIC, INC., Marlborough, MA (US)

(72) Inventors: John Laviola, Marlborough, MA (US); Shawn St. Pierre, Marlborough, MA (US); Brian Stellmach, Marlborough, MA (US); Lori Fontaine, Marlborough, MA (US); Joseph A. Stand, III, Marlborough, MA (US); Estefania Alvarez, Marlborough, MA (US); Stephen Grantz, Marlborough, MA (US); Michelle Dawn Lyman, Marlborough, MA (US); Shannon Marie Butler, Marlborough, MA (US); Yuliya Mathis, Marlborough, MA (US)

(73) Assignee: Hologic, Inc., Marlborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/524,590

(22) Filed: Nov. 11, 2021

(65) Prior Publication Data
US 2022/0061931 A1    Mar. 3, 2022

Related U.S. Application Data

(63) Continuation of application No. 16/771,379, filed as application No. PCT/US2018/065010 on Dec. 11, 2018, now Pat. No. 11,234,772.
(Continued)

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/065* (2013.01); *A61B 8/0841* (2013.01); *A61B 8/085* (2013.01);
(Continued)

(58) Field of Classification Search
CPC ........................ A61B 2034/2065; A61B 90/39
See application file for complete search history.

(56) References Cited

U.S. PATENT DOCUMENTS 6,161,034 A    12/2000  Burbank et al.
6,228,055 B1    5/2001  Foerster
(Continued)

FOREIGN PATENT DOCUMENTS

CN    1672032 A    9/2005
CN    1802125 A    7/2006
(Continued)

OTHER PUBLICATIONS

European partial Search Report in Application 18887650.2, mailed Aug. 10, 2021, 16 pages.
(Continued)

*Primary Examiner* — Amelie R Davis
(74) *Attorney, Agent, or Firm* — Merchant & Gould P.C.

(57) ABSTRACT

Disclosed biopsy markers are adapted to serve as localization markers during a surgical procedure. Adaptation includes incorporation of materials detectable under ultrasound during surgery, as well as features for co-registration with image guidance or other real-time imaging technologies during surgery. Such biopsy markers, when used as localization markers, improve patient comfort and reduce challenges in surgical coordination and surgery time. Additional disclosed biopsy markers are adapted to serve as monitoring and/or detection apparatuses. Localization of an implanted marker may be done with ultrasound technology.

(Continued)

US 12,133,695 B2

Page 2

Ultrasound image data is analyzed to identify the implanted marker. A distance to the marker or a lesion may be determined and displayed. The determined distance may be a distance between the ultrasound probe and the marker or lesion, a distance between the marker or lesion and an incision instrument, and/or a distance between the ultrasound probe and the incision instrument.

22 Claims, 22 Drawing Sheets

Related U.S. Application Data

(60) Provisional application No. 62/597,379, filed on Dec. 11, 2017, provisional application No. 62/654,071, filed on Apr. 6, 2018, provisional application No. 62/660,743, filed on Apr. 20, 2018.

(51) Int. Cl.
| | |
|---|---|
| A61B 8/00 | (2006.01) |
| A61B 8/08 | (2006.01) |
| A61B 17/3211 | (2006.01) |
| A61B 90/00 | (2016.01) |
| G06T 7/70 | (2017.01) |
| A61B 5/00 | (2006.01) |
| A61B 5/145 | (2006.01) |
| A61B 17/00 | (2006.01) |
| A61B 18/00 | (2006.01) |
| A61B 34/00 | (2016.01) |

(52) U.S. Cl.
CPC ............. *A61B 8/4254* (2013.01); *A61B 8/46* (2013.01); *A61B 8/463* (2013.01); *A61B 8/481* (2013.01); *A61B 17/3211* (2013.01); *A61B 90/39* (2016.02); *G06T 7/70* (2017.01); *A61B 5/14503* (2013.01); *A61B 5/4842* (2013.01); *A61B 8/0825* (2013.01); *A61B 2017/00867* (2013.01); *A61B 2017/00964* (2013.01); *A61B 2018/00595* (2013.01); *A61B 2034/2063* (2016.02); *A61B 2034/2065* (2016.02); *A61B 34/25* (2016.02); *A61B 2090/378* (2016.02); *A61B 2090/3904* (2016.02); *A61B 2090/3908* (2016.02); *A61B 2090/3912* (2016.02); *A61B 2090/3925* (2016.02); *A61B 2090/395* (2016.02); *A61B 2090/3995* (2016.02); *G06T 2207/10132* (2013.01); *G06T 2207/20081* (2013.01); *G06T 2207/30096* (2013.01); *G06T 2207/30204* (2013.01)

(56) References Cited

U.S. PATENT DOCUMENTS

| | | | |
|---|---|---|---|
| 6,234,177 | B1 | 5/2001 | Barsch |
| 6,436,120 | B1 | 8/2002 | Meglin |
| 8,401,622 | B2 | 3/2013 | Talpade et al. |
| 9,433,390 | B2 | 9/2016 | Nathaniel |
| 9,669,113 | B1 | 6/2017 | Sirimanne et al. |
| 9,713,437 | B2 | 7/2017 | Fullerton |
| 11,234,772 | B2 | 2/2022 | Laviola |
| 2002/0151797 | A1 | 10/2002 | Montegrande |
| 2003/0192557 | A1 | 10/2003 | Krag et al. |
| 2003/0228044 | A1 | 12/2003 | Gopalasamy |
| 2004/0236211 | A1 | 11/2004 | Burbank |
| 2005/0152588 | A1 | 7/2005 | Yoshida et al. |
| 2005/0215874 | A1 | 9/2005 | Wang et al. |
| 2006/0009696 | A1 | 1/2006 | Hanover et al. |
| 2006/0030847 | A1 | 2/2006 | McGuckin, Jr. |
| 2007/0239016 | A1 | 10/2007 | Fisher |
| 2007/0250102 | A1 | 10/2007 | Makower et al. |
| 2008/0097199 | A1 | 4/2008 | Mullen |
| 2008/0281190 | A1* | 11/2008 | Petcavich ............. A61B 90/98 600/427 |
| 2009/0131825 | A1 | 5/2009 | Burbank et al. |
| 2010/0022871 | A1 | 1/2010 | De Beni |
| 2010/0030072 | A1 | 2/2010 | Casanova et al. |
| 2010/0063392 | A1 | 3/2010 | Nishina |
| 2010/0204570 | A1 | 8/2010 | Lubock |
| 2010/0246767 | A1 | 9/2010 | Tanabe |
| 2010/0305430 | A1* | 12/2010 | Troesken ............... A61B 34/20 340/8.1 |
| 2011/0130659 | A1 | 6/2011 | Cinquin et al. |
| 2011/0313288 | A1 | 12/2011 | Chi Sing |
| 2011/0319746 | A1* | 12/2011 | Kochba ................ A61B 5/4848 600/407 |
| 2012/0265296 | A1 | 10/2012 | McNamara et al. |
| 2013/0184571 | A1 | 7/2013 | Wilkening |
| 2013/0345525 | A1* | 12/2013 | Kline .................... A61B 5/036 600/377 |
| 2014/0364728 | A1 | 12/2014 | Hashimoto |
| 2015/0196369 | A1* | 7/2015 | Glossop ................. A61B 8/12 600/417 |
| 2015/0294495 | A1 | 10/2015 | Nielsen et al. |
| 2016/0128668 | A1 | 5/2016 | Jain |
| 2016/0310760 | A1* | 10/2016 | Bharat ................. A61N 5/1038 |
| 2017/0011516 | A1* | 1/2017 | Snook .................. A61B 8/5223 |
| 2017/0202635 | A1 | 7/2017 | Ramos |
| 2017/0213358 | A1 | 7/2017 | Furuichi |
| 2018/0055476 | A1 | 3/2018 | Pizzatola et al. |
| 2018/0103912 | A1 | 4/2018 | Canfield et al. |
| 2018/0104008 | A1 | 4/2018 | Dickhans |
| 2018/0140260 | A1 | 5/2018 | Taguchi |
| 2019/0110858 | A1 | 4/2019 | Stubbs |
| 2019/0201160 | A1 | 7/2019 | Hornscheidt |
| 2021/0169579 | A1 | 6/2021 | Laviola |
| 2022/0039878 | A1 | 2/2022 | Laviola |
| 2022/0039879 | A1 | 2/2022 | Laviola |
| 2022/0061930 | A1 | 3/2022 | Laviola |
| 2022/0071714 | A1 | 3/2022 | Laviola |
| 2022/0110699 | A1 | 4/2022 | Laviola |

FOREIGN PATENT DOCUMENTS

| | | |
|---|---|---|
| CN | 101951840 A | 1/2011 |
| CN | 103547902 A | 1/2014 |
| CN | 104540447 A | 4/2015 |
| JP | 2002065876 A | 3/2002 |
| JP | 4418888 B1 | 2/2010 |
| WO | 01/08578 | 2/2001 |
| WO | 2013/096766 | 6/2013 |
| WO | 2013/163381 | 10/2013 |
| WO | 2015/138795 | 9/2015 |

OTHER PUBLICATIONS

PCT International Search Report and Written Opinion in International Application PCT/US2018/065010, mailed Jul. 23, 2019, 18 pages.
PCT International Preliminary Repoon Patentability in International Application PCT/US2018/065010, mailed Jun. 25, 2020, 14 pages.
European Extended Search Report in Application 18887650.2, mailed Nov. 11, 2021, 14 pages.
European Search Report in Application 22200406.1, mailed Jan. 19, 2023, 12 pages.

* cited by examiner

ULTRASOUND LOCALIZATION SYSTEM WITH ADVANCED BIOPSY SITE MARKERS

RELATED APPLICATIONS

This application is a continuation of U.S. patent application Ser. No. 16/771,379, now U.S. Pat. No. 11,234,772, filed Jun. 10, 2020, which is a 35 U.S.C. § 371 National Stage Application of PCT/US2018/065010 filed on Dec. 11, 2018, which claims priority to U.S. Provisional Patent Application No. 62/597,379, titled "Marker Localization Using Ultrasound" and filed on Dec. 11, 2017; U.S. Provisional Patent Application No. 62/660,743, titled "Ultrasound Localization System" and filed on Apr. 20, 2018; and U.S. Provisional Patent Application No. 62/654,071, titled "Advanced Biopsy Markers" and filed on Apr. 6, 2018. Each of these applications are incorporated herein by reference in their entireties. To the extent appropriate, a claim of priority is made to each of the above disclosed applications.

BACKGROUND

In the diagnosis of breast cancer, a suspicious mass may be discovered during a preliminary examination involving visual examination, palpation, ultrasonic imaging, x-ray, magnetic resonance imaging (MRI), or other detection means. Thereafter, a biopsy procedure may be performed to determine whether the suspicious mass is malignant or benign. To minimize surgical intrusion, the biopsy procedure may involve inserting a small biopsy needle into the breast to extract one or more samples (e.g., five samples) from locations around the mass and from the center of the mass. In one biopsy procedure, an ultrasound transducer is positioned on the breast, typically with one hand and used to provide visual guidance to the medical professional performing the biopsy. A biopsy needle held in the other hand of the medical professional is inserted it to the lesion location.

Regardless of the imaging modality or instrument used to perform the biopsy procedure, subsequent examination of the biopsy site may be necessary, either in a follow up screening examination or for treatment of a cancerous lesion. In order to mark the location of the lesion for subsequent examination or treatment, a "biopsy site marker" may be surgically inserted during the biopsy procedure.

In its simplest form, a biopsy site marker serves as a landmark for future identification of a position of the lesion for treatment or further examination and is the standard of care for breast biopsy. However, due to limited advances in materials technology selection, manufacturing and deployment, paired with the high skill needed to identify markers under different imaging modalities, traditional biopsy site markers suffer from a number of deficiencies, including poor detection under ultrasound or other visualization modalities, inability to co-register with surgical imaging modalities (e.g., an in-room image guidance system, magnetic resonance imaging (MRI), etc.), lack of on-going lesion monitoring capabilities, and lack of differentiation between the biopsy site marker and anatomical features of the patient.

If the biopsied site is cancerous, treatments may include mastectomy, lumpectomy, radiation therapy, or chemotherapy procedure that require the surgeon or radiologist to direct surgical or radiation treatment to the precise location of the lesion. Surgical resection is the gold standard, with more than 50% of cancer patients having surgical procedures. There are few successful technologies, and these are primarily conducted ex vivo outside of the cavity, for determining the margin of a tumor (which happens mostly ex vivo outside of the cavity), which includes a rim of normal tissue surrounding the tumor. Ideally during resection, the surgeon intends to have 'clear' margins, i.e., the complete tumor surrounded by healthy tissue. Even so, upon removal, the surgeon stains the resected tumor and sends it for frozen section to be assessed by a pathologist regarding whether the margins are actually clear or whether more tissue should be removed in a specific orientation. In aspects, such resection may occur days or weeks after the biopsy procedure, by which time the original features of the tissue may have been removed or altered by the biopsy or may have changed due to growth or progress of the lesion.

In order to mark the location of the lesion for resection, an additional localization procedure is performed prior to resection. With respect to localization, the patient must undergo an additional procedure, prior to surgery, to insert a breast lesion localization wire at the biopsy site. The surgeon then uses the localization wire to advance to the cutting instrument to the site of the lesion to remove the lesion. Generally, an interventional radiologist is required to deploy the wire under an imaging modality just prior to surgery, for example x-ray. However, localization wires are not only uncomfortable but can also dislodge or move as the stainless steel wire is protruding from the patient prior the procedure. In addition, the use of a wire causes significant logistical issues for the medical facility. For instance, a radiologist must be available at a time slot directly prior to when a surgeon is available to perform the surgery. Such scheduling requirements are often difficult to achieve, and radiologists and surgeons may also be located in different buildings of a medical campus. In addition to the above deficiencies, traditional biopsy site markers are ill-equipped to monitor the progression or regression of a lesion before, during or after a surgical procedure or other treatment.

Wireless localization systems, such as radio frequency guided localization, electromagnetic reflectors, magnetic tracers, and radioactive seed, are known, but suffer from a number of drawbacks. All of which although may reduce patient discomfort, suffer the drawback of having an additional step in the surgical workflow.

If the breast radiologist feels there is a chance that a finding on diagnostic breast imaging is cancer, an image-guided breast biopsy will be suggested. The current standard of care at the completion of a biopsy recommends placement of a biopsy marker into the biopsied site. There are different types of biopsy markers but some are made of materials that have greater visibility under ultrasound than others. The marker serves multiple purposes. First, the marker serves to mark where the tissue was sampled in the breast. If the original area of interest is no longer visible by imaging after the biopsy, the marker is a guide to know where the diseased tissue was sampled. Second, if surgery is recommended, the marker can be used as a target for the radiologist to place the localization wire to the location of the marker. Third, the cancerous mass including the marker (and wire) removed during surgery may then be imaged to ensure that the correct to show the mass was accurately removed from the breast.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for the localization of an implanted marker through ultrasound technology along with additional combinations of other modalities.

In aspects, a first biopsy marker is provided. The biopsy marker includes a central orb and a plurality of radial spokes connected at a proximal end to the central orb, where each of the plurality of radial spokes terminates at a distal orb. At least one of the plurality of radial spokes is selectively positionable in a condensed configuration and in an expanded configuration. When in the condensed configuration, at least one of the plurality of radial spokes is folded in lateral alignment with a surface of the central orb; and when in the expanded configuration, at least one of the plurality of radial spokes protrudes radially from the surface of the central orb. The biopsy marker is configured for insertion at a biopsy site in the condensed configuration and is configured to deploy from the condensed configuration to the expanded configuration upon insertion at a biopsy site. In some cases, the biopsy marker is configured to deploy into the expanded configuration based at least in part on shape-memory properties of a material from which the biopsy marker is made. The material may be an alloy capable of reflecting ultrasound waves, such as Nitinol. Additionally, the biopsy marker may be configured for localization using ultrasonic imaging. In some cases, at least one distal orb of the biopsy marker includes a contrasting agent, which is configured to be released into a biopsy site when impacted by ultrasound waves.

In further aspects, a second biopsy marker is provided. The biopsy marker includes a central core formed of a first material and at least a first layer formed of a second material and surrounding the central core. In some cases, the second material may be configured to be activated by ultrasound waves; and in other cases, the second material may include a chemotherapeutic drug that may be configured to become soluble when impacted by ultrasound waves. Alternatively, the second material may include a cancer-binding agent that is configured to be released when the second material is impacted by ultrasound waves. Alternatively still, the second material may include a rare earth magnetic metal that is configured to be activated by ultrasound waves, an ingested agent, or an external remote control. When the second material is activated, the biopsy marker may be configured to alter a shape. In other case, the second material may be configured to be activated by one or more changes in a bio-environment, such as a change in pH, a change in temperature, or a change in electrolyte concentration. In response to one or more changes in the bio-environment, the second material may be configured to exhibit increased fluoresce, increased solubility, increased echogenicity, a release of a contrasting agent, or a release of a chemotherapeutic drug. When the central core is spherical, the second material may form a concentric layer surrounding the central core. Additionally, a second layer formed of a third material may surround the first layer. The third material may be different than the second material. In some aspects, the biopsy marker may be configured for localization under ultrasonic imaging.

Further still, a third biopsy marker is provided. The biopsy marker includes a fibrous polymer configured to be reactive to one or more conditions of a bio-environment surrounding the fibrous polymer. The one or more conditions of the bio-environment may include one or more of: a temperature, a pH, an electrolyte concentration and a blood flow. The fibrous polymer may be configured to react to a condition of the bio-environment by one of: emitting heat, emitting visible light, fluorescing, increasing echogenicity, vibrating, shortening, lengthening, folding and thickening. In an example when the fibrous polymer reacts by emitting heat, thermographic imaging of the biopsy marker may generate a heat map that may be indicative of a margin of the lesion. In aspects, the biopsy marker is configured to be injected near a lesion of a patient during a biopsy procedure.

In additional aspects, a method of determining information regarding a lesion from a biopsy marker is provided. The method includes implanting the biopsy marker during a biopsy procedure and activating the biopsy marker, where activating the biopsy marker may include delivering an agent to the biopsy marker, impacting the biopsy marker by ultrasound waves, or activating the biopsy marker using an external device. The biopsy marker may be activated in response to a change in a bio-environment, where the change in the bio-environment may include a change in pH, a change in temperature, a change in blood flow or a change in electrolyte concentration. In aspects, the change in bio-environment may be indicative of a change in the lesion. The method further includes receiving data from the biopsy marker and analyzing the received data, where analyzing the received data may include determining a location and/or an orientation of the biopsy marker. In some cases, determining the location and/or orientation of the biopsy marker may be performed during a surgical procedure subsequent to the biopsy procedure. Based on the analyzed data, the method includes determining information regarding the lesion, where determining information regarding the lesion may include determining whether the lesion is progressing or regressing or determining a margin of the lesion.

In an aspect, the technology relates to a method for localization of an implanted marker with ultrasound technology. The method includes emitting an array of ultrasonic sound waves from an ultrasonic transducer of an ultrasound probe; detecting reflected ultrasonic sound waves by the ultrasonic transducer, wherein the reflected ultrasonic sound waves include at least a portion of the array of ultrasonic sound waves after being reflected from a marker implanted proximate a lesion within an interior of a patient; and generating image data from the reflected ultrasonic sound waves. The method also includes analyzing, by a processor, the generated image data to identify the marker within the interior of the patient; based at least in part on the identification of the marker, determining, by the processor, a distance to at least one of the marker or the lesion; and displaying, on a display operatively connected to the processor, the determined distance to the at least one of the marker or the lesion.

In an example, the method includes displaying, on the display, an ultrasound image including the marker based on the reflected ultrasonic sound waves. In another example, the determined distance to the at least one of the marker or the lesion is displayed concurrently with the ultrasound image. In yet another example, the marker is visually distinguished from a remainder of the ultrasound image by at least one of: highlighting, outlining, a displayed indicator, or a color effect. In still another example, the determined distance to the at least one of the marker or the lesion is one of: a distance from a portion of the ultrasound probe to the at least one of the marker or the lesion, a distance from a portion of a scalpel to the at least one of the marker or the lesion, or a distance from a portion of an incision instrument to the at least one of the marker or the lesion. In still yet another example, the incision instrument is one of a cautery tool, a scalpel, or an internal probe.

In another example, the method includes receiving a signal from a marker localization transceiver, wherein the marker localization transceiver is attached to the marker; processing, by the processor, the signal received from the marker localization transceiver to determine at least one of a location of the marker or an orientation of the marker; and wherein determining the distance to the at least one of the marker or the lesion is further based on the at least one of the location of the marker or the orientation of the marker. In yet another example, the method includes receiving a signal from a probe localization transceiver, wherein the probe localization transceiver is attached to the ultrasound probe; processing, by the processor, the signal received from the probe localization transceiver to determine at least one of a location of the ultrasound probe or an orientation of the ultrasound probe; and wherein determining the distance to the at least one of the marker or the lesion is further based on the at least one of the location of the ultrasound probe or the orientation of the ultrasound probe. In still another example, the method includes receiving a signal from an instrument localization transceiver, wherein the instrument localization transceiver is attached to an incision instrument; processing, by the processor, the signal received from the instrument localization transceiver to determine at least one of a location of the incision instrument or an orientation of the incision instrument; and wherein determining the distance to the at least one of the marker or the lesion is further based on the at least one of the location of the ultrasound probe or the orientation of the ultrasound probe.

In another example, the determined distance includes a directional component. In yet another example, analyzing, by a processor, the generated image data to identify the marker within the interior of the patient further comprises analyzing the generated image data using pattern recognition techniques to identify the marker based on a cross-section of the marker. In still another example, the analyzing, by a processor, the generated image data to identify the marker further comprises identifying an orientation of the marker based on a cross-section of the marker. In still yet another example, the determining a distance to the marker within the interior of the patient is further based on the identified orientation of the marker.

In another aspect, the technology relates to a method for localization of an implanted marker with ultrasound technology. The method includes emitting a first array of ultrasonic sound waves from an ultrasonic transducer of an ultrasound probe in a first position; detecting first reflected ultrasonic sound waves by the ultrasonic transducer, wherein the first reflected ultrasonic sound waves include at least a portion of the first array of ultrasonic sound waves after being reflected from a marker implanted within an interior of a patient; generating first image data from the first reflected ultrasonic sound waves. The method also includes analyzing, by a processor, the generated first image data to identify the marker within the interior of the patient. The method further includes emitting a second array of ultrasonic sound waves from the ultrasonic transducer of the ultrasound probe in a second position; detecting second reflected ultrasonic sound waves by the ultrasonic transducer, wherein the second reflected ultrasonic sound waves include at least a portion of the second array of ultrasonic sound waves after being reflected from within the interior of the patient; generating second image data from the first reflected ultrasonic sound waves; and analyzing, by the processor, the generated second image data to determine the marker is not present within the generated second image data. The method further includes generating a navigation indicator, wherein the navigation indicator indicates a direction of the marker relative to the second position of the ultrasound probe; and displaying the navigation indicator on a display concurrently with an ultrasound image generated from the second image data.

In an example, the method includes generating a first image from the first image data; and displaying the first image on a display operatively connected to the processor. In another example, the method includes based at least in part on the identification of the marker in the generated first image data, determining a distance to the marker within the interior of the patient; and displaying on the display, concurrently with the display of the first image, the determined distance to the marker. In yet another example, the determined distance to the marker is one of: a distance from a portion of the ultrasound probe to the marker, a distance from a portion of a scalpel to the marker, or a distance from a portion of a cautery tool to the marker. In still another example, the navigation indicator is an arrow pointing in the direction of the marker relative the second position of the ultrasound probe. In still yet another example, the method includes receiving a signal from a marker localization transceiver, wherein the marker localization transceiver is attached to the marker; processing, by the processor, the signal received from the marker localization transceiver to determine at least one of a location of the marker or an orientation of the marker; and wherein generating the navigation indicator is further based on the at least one of the location of the marker or the orientation of the marker. In another example, the method includes receiving a signal from a probe localization transceiver, wherein the probe localization transceiver is attached to the ultrasound probe; processing, by the processor, the signal received from the probe localization transceiver to determine at least one of a location of the ultrasound probe or an orientation of the ultrasound probe; and wherein generating the navigation indicator is further based on the at least one of the location of the ultrasound probe or the orientation of the ultrasound probe.

In another aspect, the technology relates to a system for ultrasound localization. The system includes an implanted marker, wherein the implanted marker is implanted in an interior of a patient; an ultrasound probe comprising an ultrasonic transducer, the ultrasonic transducer configured to emit an array of ultrasonic sound waves and detect reflected ultrasonic sound waves, wherein the reflected ultrasonic sound waves include at least a portion of the array of ultrasonic sound waves after being reflected within an interior of a patient; a display; at least one processor operatively connected to the display and the ultrasound probe; and memory, operatively connected to the at least one processor, storing instructions that when executed by the at least one processor perform a set of operations. The set of operations includes generating image data from the reflected ultrasonic sound waves; analyzing, by a processor, the generated image data to identify the marker within the interior of the patient; based on the identification of the marker and the reflected ultrasonic sound waves, determining a distance to at least one of the marker or the lesion; and displaying, on the display, the determined distance to the at least one of the marker or the lesion.

In an example, the system also includes a marker localization transceiver attached to the marker, wherein the marker localization transceiver transmits data to indicate at least one of a location of the marker or an orientation of the marker. In another example, the system also includes a probe localization transceiver attached to the ultrasound probe, wherein the probe localization transceiver transmits data to indicate at least one of a location of the probe or an orientation of the probe. In still another example, the system includes an incision instrument, wherein the incision instrument includes an instrument localization transceiver, wherein the instrument localization transceiver transmits data to indicate at least one of a location of the incision instrument or an orientation of the incision instrument. In yet another example, the incision instrument is one of a cautery tool, a scalpel, or an internal probe. In still yet another example, the instrument localization transceiver is attached to a tip of the incision instrument.

In another example, at least one of the marker localization transceiver, the probe localization transceiver, or the instrument localization transceiver is a radio-frequency identification (RFID) device. In still another example, the system further comprises an inductive power source, wherein at least one of the marker localization transceiver, the probe localization transceiver, or the instrument localization transceiver is powered by the inductive power source.

In another aspect, the technology relates to a method for ultrasound localization and navigation. The method includes emitting an array of ultrasonic sound waves from an ultrasonic transducer of an ultrasound probe; detecting reflected ultrasonic sound waves by the ultrasonic transducer, wherein the reflected ultrasonic sound waves include at least a portion of the array of ultrasonic sound waves after being reflected from an interior of a patient having an implanted marker proximate a lesion; generating image data from the reflected ultrasonic sound waves; and analyzing, by a processor, the generated image data to determine whether the marker is present in the image data. The method further includes based on the determination of whether the marker is present in the image data, perform at least one of: if the marker is present in the image data: determining, by the processor, a distance to at least one of the marker or the lesion; and displaying, on a display operatively connected to the processor, the determined distance to the at least one of the marker or the lesion; and if the marker is not present in the image data: determining the location of the marker; generating a navigation indicator, wherein the navigation indicator indicates the location of the marker relative to a current position of the ultrasound probe; and displaying the navigation indicator on the display concurrently with an ultrasound image.

In another aspect, the technology relates to a method for localization of an implanted marker with ultrasound technology. The method includes emitting an array of ultrasonic sound waves from an ultrasonic transducer of an ultrasound probe; detecting reflected ultrasonic sound waves by the ultrasonic transducer, wherein the reflected ultrasonic sound waves include at least a portion of the array of ultrasonic sound waves after being reflected from a marker implanted proximate a lesion within an interior of a patient; generating image data from the reflected ultrasonic sound waves; displaying an ultrasound image from the generated image data; receiving user input to identify the marker in the ultrasound image; based at least in part on the identification of the marker, determining, by the processor, a distance to at least one of the marker or the lesion; and displaying, on a display operatively connected to the processor, the determined distance to the at least one of the marker or the lesion.

In an example, the method further includes identifying an incision instrument in the ultrasound image. In yet another example, identifying the incision instrument in the ultrasound image is based on user input identifying the incision instrument. In still another example, the method further includes receiving input identifying a type of the incision instrument. In yet another example, identifying the incision instrument in the ultrasound image is based on the type of the incision instrument. In still yet another example, the method further includes receiving input regarding a type of the marker. In another example, the determined distance is a distance between the incision instrument and the marker. In yet another example, determining the distance is based on user input drawing line between the incision instrument and the marker on the ultrasound image.

In another aspect, the technology relates to a method for confirming margins of a specimen. The method includes imaging the specimen from a first orientation with an ultrasound probe, wherein the specimen includes a lesion; determining the location of the lesion in the first orientation; based on the location of the lesion, determining that a margin between the lesion and the edge of the specimen in the first orientation is less than a predetermined margin; based on the margin being less than the predetermined margin, generating an alert. In an example, determining the location of the lesion includes determining a distance from the ultrasound probe to the lesion. In another example, determining that the margin between the lesion and the edge of the specimen in the first orientation includes comparing the location of the of the lesion to a predicted location of the lesion in the first orientation. In yet another example, determining that the margin between the lesion and the edge of the specimen in the first orientation includes determining a difference between a distance from the ultrasound probe to the lesion and a distance from the lesion to a surface on which the lesion is placed. In still another example, the method further includes rotating at least one of the specimen and the ultrasound probe; imaging the specimen from a second orientation with the ultrasound probe; determining the location of the lesion in the second orientation; based on the location of the lesion, determining that a margin between the lesion and the edge of the specimen in the second orientation is less than the predetermined margin; based on the margin being less than the predetermined margin, generating another alert.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1A:
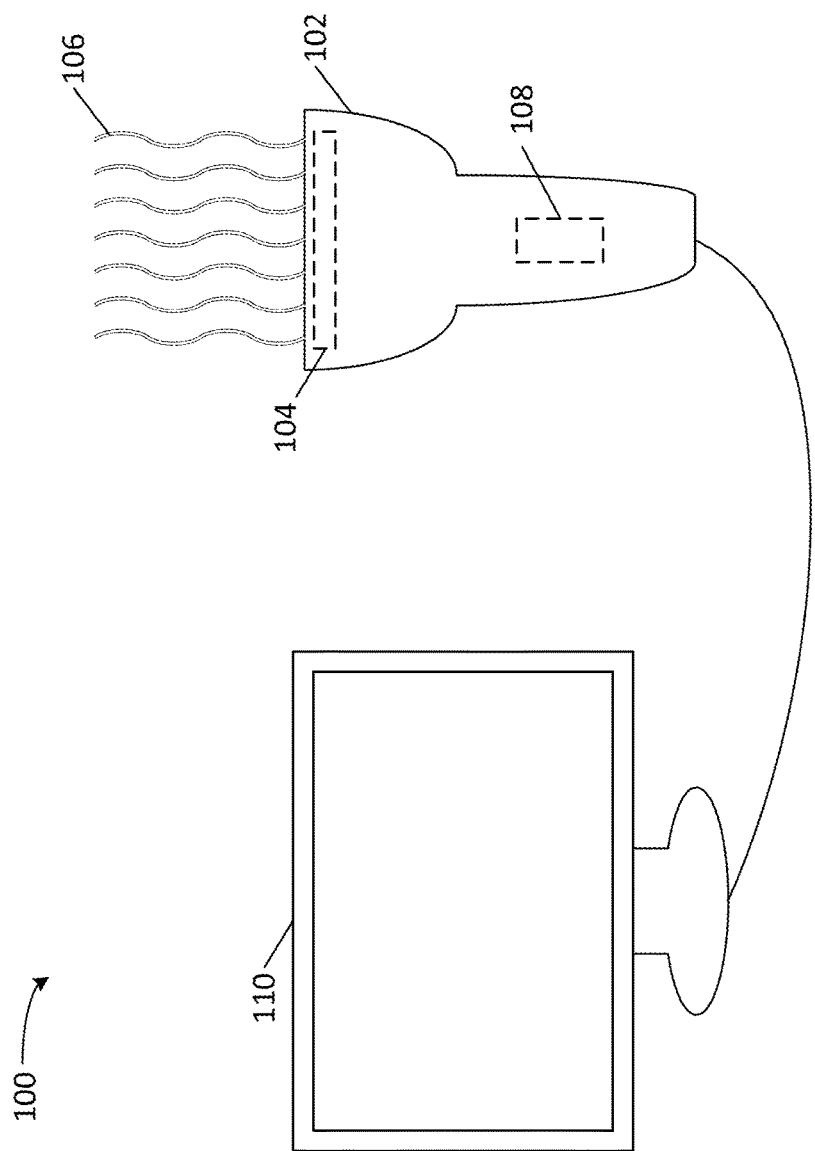
FIG. 1A depicts an example of an ultrasound localization system.

As discussed above, with respect to localization, the patient must generally undergo an additional procedure to insert a breast lesion localization wire at the biopsy site. As detailed above, localization wires are not only uncomfortable for the patient but cause significant logistical issues for the medical facility.

As described herein, biopsy markers may be adapted to serve as localization markers during a surgical procedure. Prior biopsy site markers serve as poor localization markers during a surgical procedure because they are not easily distinguished weeks or months after placement and are ill-equipped to monitor the progression or regression of a lesion before, during or after a surgical procedure or other treatment. The adaptation of biopsy site markers for localization may include incorporation of various materials that are detectable under ultrasound during surgery, as well as features for co-registration with image guidance or other real-time imaging technologies during surgery. In this way, the use of biopsy markers, which are inserted with minimal intervention many days or weeks prior to a surgical procedure, improve patient comfort and reduce challenges in surgical coordination and patient time in surgery. Precise localization of the marker (e.g., placement within 1 centimeter of the lesion) can increase the healthy tissue left behind after removal of the tumor, whereas if the marker is displaced by even a few millimeters or centimeters from the correct lesion, it can cause excessive tissue removal leading to additional surgeries for complete removal or for optimizing cosmetic outcomes.

Additionally or alternatively, biopsy markers may be adapted to serve as monitoring and/or detection apparatuses. For example, biopsy markers may be equipped with a radio frequency identification (RFID) chip for sending and receiving data, global positioning (GPS) functionality for detecting real-time marker positioning, features for co-registration within a surgical room imaging field, pH meter or pH-reactive material, a magnetic seed or radioactive material contained within it, movement detection functionality (e.g., via Doppler), vibration detection functionality (e.g., via ultrasound elastography), thermal detection functionality or a thereto-reactive material, electrolyte monitoring functionality, tumor recognition functionality (e.g., via antigen binding, secretion detection, blood-flow or blood-pressure monitoring, etc.), and the like. It is with respect to these and other biopsy marker advances that the present disclosure is directed.

In addition, prior solutions to localization of lesions through the use of stainless steel wires have several disadvantages ranging from patient discomfort to medical facility logistics. As an example, the use of a stainless steel wire requires substantial additional medical facility utilization on the day of surgery. For instance, on the day of surgery, a patient and any imaging modalities must first be prepped in radiology. A radiologist must then be available to insert the wire under the imaging modality. Once the wire is inserted, it may need to be further imaged and secured to allow transfer of the patient to the operating room. After the patient is transferred to the operating room, the surgeon is still unable to view a live visualization of the lesion. Instead, the surgeon is required to rely solely on the wire as a guide to the lesion. Even where non-wire solutions are implemented, such as the use of a radioactive seed, a radiologist is still generally required for insertion of the seed. In addition, the radioactive seed also introduces radiation into the patient. Similarly, other non-wire solutions such as radio frequency guided, electromagnetic reflectors, and magnetic tracers also require the radiologist's time for the placement of the non-wire technology prior to surgery.

Examples of the present technology improve upon the prior technology requiring a wire, by allowing a marker to be implanted at the lesion site multiple days prior to a surgery as well as providing a live visualization and localization of the marker during surgery. For example, the marker can be placed at the time of a biopsy, rather than near the time of surgery. Further, a radiologist may no longer be needed in a pre-surgical procedure to place the wire or wireless localization device. At the time of surgery, the surgeon is also able to obtain a visualization of the marker through the use of ultrasound.

For example, an ultrasound imaging system can detect and identify the marker within the patient. Upon identification of the marker, a distance and/or direction to the marker can be automatically determined and displayed to the surgeon along with an ultrasound image. The distance and direction to the marker may be indicative of a distance from an ultrasound probe to the marker or a distance from a marker to an incision instrument, such as a cautery tool, scalpel, or internal probe. In addition, where the geometry of the marker and the geometry of the lesion are known, a distance to an edge of the lesion may also be generated. Accordingly, the surgeon is able to more accurately perform the surgical incisions to get to a lesion marked by the marker.

FIG. 1A depicts an example of an ultrasound localization system 100. The ultrasound localization system 100 includes an ultrasound probe 102 that includes an ultrasonic transducer 104. The ultrasonic transducer 104 is configured to emit an array of ultrasonic sound waves 106. The ultrasonic transducer 104 converts an electrical signal into ultrasonic sound, or ultrasound, waves 106. The ultrasonic transducer 104 may also be configured to detect ultrasonic sound waves, such as ultrasonic sound waves that have been reflected from internal portions of a patient. In some examples, the ultrasonic transducer 104 may incorporate a capacitive transducer and/or a piezoelectric transducer, as well as other suitable transducing technology.

The ultrasonic transducer 104 is also operatively connected (e.g., wired or wirelessly) to a display 110. The display 110 may be a part of a computing system, including processors and memory configured to produce and analyze ultrasound images. Further discussion of a suitable computing system is provided below with reference to FIG. 1E. The display 110 is configured to display ultrasound images based on an ultrasound imaging of a patient. The ultrasound imaging performed in the ultrasound localization system 100 is primarily B-mode imaging, which results in a two-dimensional ultrasound image of a cross-section of a portion of the interior of a patient. The brightness of the pixels in the resultant image generally corresponds to amplitude or strength of the reflected ultrasound waves. Other ultrasound imaging modes may also be utilized.

The ultrasound probe 102 may also include a probe localization transceiver 108. The probe localization transceiver 108 is a transceiver that emits a signal providing localization information for the ultrasound probe 102. The probe localization transceiver 108 may include a radio frequency identification (RFID) chip or device for sending and receiving information. For instance, the signal emitted by the probe localization transceiver 108 may be processed to determine the orientation or location of the ultrasound probe 102. The orientation and location of the ultrasound probe 102 may be determined or provided in three-dimensional components, such as Cartesian coordinates or spherical coordinates. The orientation and location of the ultrasound probe 102 may also be determined or provided relative to other items, such as an incision instrument, a marker, a magnetic direction, a normal to gravity, etc. With the orientation and location of the ultrasound probe 102, additional information can be generated and provided to the surgeon to assist in guiding the surgeon to a lesion within the patient, as described further below. While the term transceiver is used herein, the term is intended to cover both transmitters, receivers, and transceivers, along with any combination thereof.

Figure 1B:
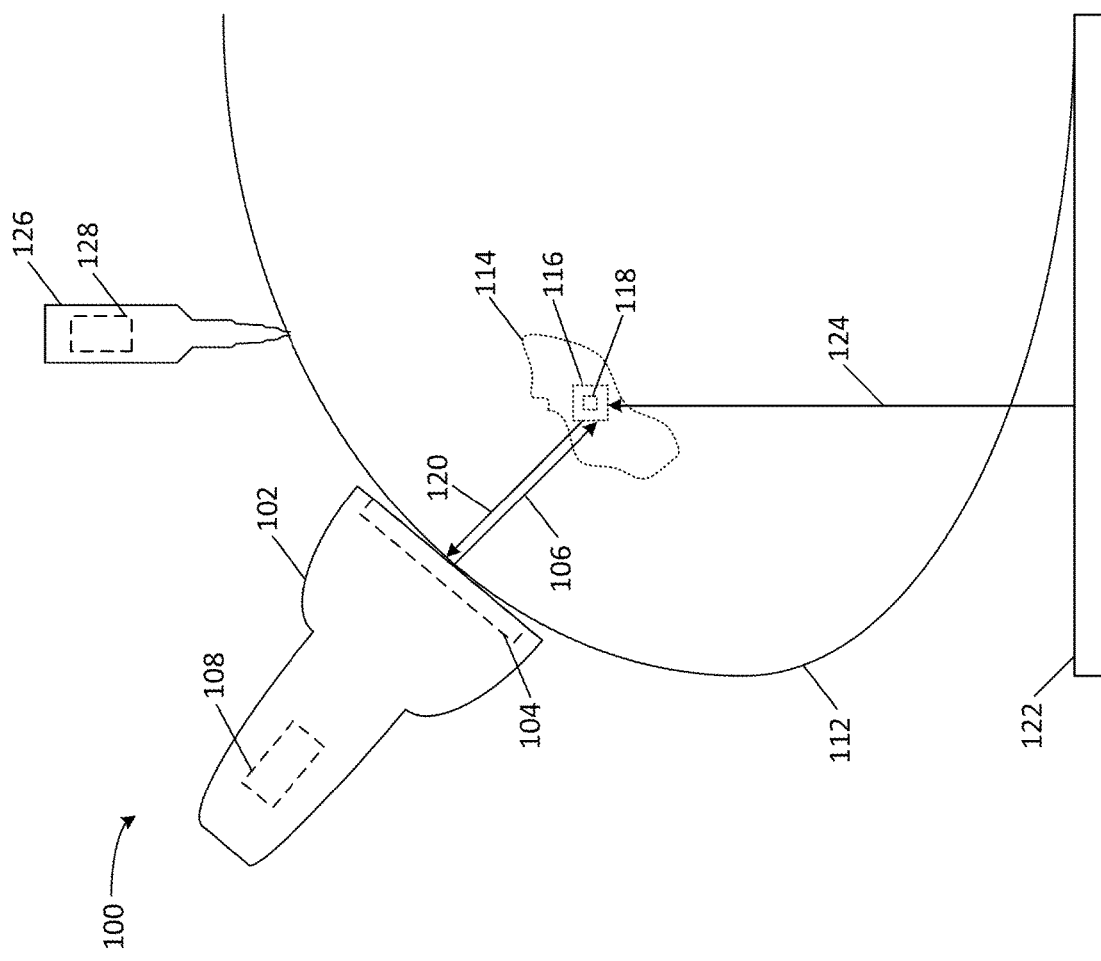
FIG. 1B depicts an example of the ultrasound localization system in use with a patient.

FIG. 1B depicts an example of the ultrasound localization system 100 in use with a patient 112. In aspects, the ultrasound localization system 100 may be utilized during a surgical procedure. In other aspects, the ultrasound localization system 100 may be utilized during an examination or diagnostic procedure. The ultrasound probe 102 is in contact with a portion of the patient 112, such as a breast of the patient 112. In the position depicted in FIG. 1B, the ultrasound probe 102 is being used to image a portion of the patient 112 containing an irregularly shaped lesion 114. A marker 116 has been implanted at or near the lesion 114. In aspects, the marker 116 may be implanted at the lesion during or in association with a biopsy procedure prior to the surgical procedure discussed herein. The marker 116 allows for the lesion 114 to be localized through the use of the ultrasound localization system 100. To image the portion of the patient 112 containing the marker 116, the ultrasonic transducer 104 emits an array of ultrasonic sound waves 106 into the interior of the patient 112. A portion of the ultrasonic sound waves 106 are reflected off internal components of the patient 112 as well as the marker 116, when the marker 116 is in the field of view, and return to the ultrasound probe 102 as reflected ultrasonic sound waves 120. The reflected ultrasonic sound waves 120 may be detected by the ultrasonic transducer 104. For instance, the ultrasonic transducer 104 receives the reflected ultrasonic sound waves 120 and converts the ultrasonic sound waves 120 into an electric signal that can be processed and analyzed to generate ultrasound image data on display 110. The depth of the marker 116 or other objects in an imaging plane may be determined from the time between a pulse of ultrasonic waves 106 being emitted from the ultrasound prove 102 and the reflected ultrasonic waves 120 being detected by the ultrasonic probe 102. For instance, the speed of sound is well-known and the effects of the speed of sound based on soft tissue are also determinable. Accordingly, based on the time of flight of the ultrasonic waves 106 (more specifically, half the time of flight), the depth of the object within an ultrasound image may be determined. Other corrections or methods for determining object depth, such as compensating for refraction and variant speed of waves through tissue, may also be implemented. Those having skill in the art will understand further details of depth measurements in medical ultrasound imaging technology.

In addition, multiple frequencies or modes of ultrasound techniques may be utilized. For instance, real time and concurrent transmit and receive multiplexing of localization frequencies as well as imaging frequencies and capture frequencies may be implemented. The localization frequencies may be implemented for lesion or marker targeting and the imaging frequencies implemented for ultrasonography. Utilization of these capabilities provide information to co-register or fuse multiple data sets from the ultrasound techniques to allow for a real-time visualization of a marker 116 and medical images on the display 110. The imaging frequencies and capture sequences may include B-mode imaging (with or without compounding), Doppler modes (e.g., color, duplex), harmonic mode, shearwave and other elastography modes, and contrast-enhanced ultrasound, among other imaging modes and techniques.

As detailed above, the marker 116 may be implanted at or near the lesion 114 prior to a surgical procedure. For instance, when the lesion was detected in patent 112, samples may have been taken by biopsy and then tested to determine whether the lesion was malignant or benign. Thereafter, if the lesion was determined to be malignant, treatment and/or further examination may have been prescribed. Such treatment, including surgical removal, radiation therapy, or other targeted therapy, may occur days or weeks after the biopsy procedure, by which time the original features of the tissue may have changed. Accordingly, the marker 116 may be inserted during the biopsy procedure for future identification of the location of the lesion 114. In this way, rather than requiring coordination and placement of a localization wire at the time of surgery, the previously-inserted marker 116 may be utilized to localize the lesion. Thus, logistics and scheduling on the day of surgery are simplified, as well as reducing an overall surgical time for the patient. Further benefits are realized because marker 116 may be specially designed for detection using ultrasound or other imaging technologies to provide live imaging and lesion location data during the surgical procedure.

In the example depicted, the marker 116 is in the shape of a cube. By utilizing a marker 116 in the shape of a cube, the marker 116 can be more easily detected in an ultrasound image because cube-shaped items should not naturally occur within the human body. For similar reasons, other shapes that are unexpected to occur in the human body may also be used for the marker 116. For example, shapes that have symmetries similar to that of a cube or an elongated rectangular prism also allow for determinations of orientation of the marker 116 based on a cross-section of the marker 116 appearing in a respective ultrasound image, as discussed in further detail below. Additionally, radially-symmetrical shapes, multi-layered spherical shapes or spherically-shaped lattice structures, none of which would be naturally occurring in the human body, could be used to differentiate the marker 116 from surrounding anatomy and/or tissue. For example, the marker 116 may be of a shape that has clear margins (the opposite of spiculated), is of homogenous echogenicity, is hyperechoic in nature, without posterior acoustic shadowing, and is wider rather than taller in appearance.

The marker 116 may also include a marker localization transceiver 118. The marker localization transceiver 118 is a transceiver that emits a signal providing localization information for the marker 116. The marker localization transceiver 118 may include a radio frequency identification (RFID) chip or device for sending and receiving information. For instance, the signal emitted by the marker localization transceiver 118 may be processed to determine the orientation or location of the marker 116. The orientation and location of the marker localization transceiver 118 may be determined or provided in three-dimensional components, such as Cartesian coordinates or spherical coordinates. The orientation and location of the marker 116 may also be determined or provided relative to other items, such as an incision instrument 126, the ultrasound probe 102, a magnetic direction, a normal to gravity, etc. With the orientation and location of the marker 116, additional information can be generated and provided to the surgeon to assist in guiding the surgeon to a lesion within the patient, as described further below.

In other aspects, marker 116 may include additional or alternative functionality. For instance, marker 116 may include one or more sensors or other detectors for monitoring the progression or regression of the tumor. For instance, such sensors may include a pH sensor, a blood-flow (or blood-pressure) sensor, an electrolyte sensor (e.g., for detecting uptake of calcium ions, Ca2+), a thermo-sensor, a Doppler device, etc. Sensors associated with or incorporated into the marker 116 may communicate sensor data with one or more devices via marker localization transceiver 118 or another transceiver (not shown). The devices for receiving the sensor data may be in communication with the localization system 100 or may be in communication with an independent monitoring system. In some cases, the monitoring system may evaluate the sensor data during a surgical procedure, on a continuous or semi-continuous basis between surgical treatments, or any combination thereof. Evaluating the sensor data may enable the monitoring system to detect changes in the tumor. For instance, an increase in blood-flow or thermographic footprint may indicate that cellular metabolism or vascularization is increasing in the area of the tumor, which may indicate a progression of the lesion. In contrast, a decrease in blood-flow or thermographic footprint may indicate a decrease in cellular metabolism or vascularization and a corresponding regression of the lesion. Additionally or alternatively, sensor data that indicates a reduction in pH, or an increase in calcium ion (Ca2+) uptake, at or near the tumor site may be indicative of tumor progression. As should be appreciated, an increase in pH and/or a decrease in calcium ion uptake at or near the tumor site may be indicative of tumor regression.

In still other aspects, marker 116 may comprise an implantable chip including hardware and/or software for monitoring a lesion size and pathology. For instance, an implantable chip marker may be configured with hardware and software for monitoring one or more of the conditions described above utilizing one or more associated sensors. Additionally or alternatively, the implantable chip marker may provide in-situ delivery of prescribed drugs or may deliver targeted radiation to a lesion. In some cases, the implantable chip marker may be activated by ultrasound waves or by an external remote control. The implantable chip marker may further include a transceiver for sending and receiving data to or from an external computing device and/or display.

In some cases, an agent may be ingested (e.g., as a pill or other formulation in the days or weeks before a surgical procedure) that scouts out and activates marker 116. For example, marker 116 may comprise a receptor surface compatible with the agent.

Upon binding to the receptor surface, the agent may activate marker 116 or the agent itself may be activated. In this way, marker 116 may serve as a localization marker when activated by the agent. Alternatively, the agent may serve as a cancer-cell binding agent. After ingestion, the agent may scout out lesion 114 (or other cancerous tumors) and may bind to the surface of lesion 114. In aspects, the agent may exhibit properties detectable by various imaging systems. For example, the agent may fluoresce, may vibrate, may emit heat or visible light, may exhibit high echogenicity, etc. In this way, the marker 116 and/or lesion 114 may be localized by an ingested agent.

In one embodiment, the marker 116 is comprised of a marker material that is substantially dehydrated in a pre-deployment configuration and that is configured to expand when exposed to fluid following deployment. The marker material may be further configured to remain substantially physically stable when implanted for an extended period of time (e.g., from the biopsy procedure until at least one subsequent surgical procedure). In addition to being formed into a recognizable shape, as detailed above, the marker material may be configured to reflect ultrasound in a way that the marker 116 is recognizable as being artificial. For example, the marker 116 may be reflective enough for detection, but may not significantly block any anatomy underneath it. For example, the ultrasound-reflective material may be Nitinol. Nitinol is an alloy comprised of nickel and titanium arranged in a crystalline lattice. The crystalline lattice exhibits an ability to exist in two different phases, known as martensite and austenite. The austenite arrangement is more compact and requires more energy to maintain so that under normal conditions Nitinol assumes the lower-energy, expanded martensite arrangement. Due at least in part to this unique property, Nitinol exhibits shape-memory properties, which enables Nitinol to be formed into a first shape at a high temperature and, upon cooling, be reformed into at least one second shape. Thereafter, when heated above a transition temperature, the Nitinol resumes the first shape. Nitinol is generally provided as a wire, which may be woven into a wire mesh, braided, or otherwise shaped or configured.

The marker 116, various sensors, and/or the marker localization transceiver 118 may be powered via an inductive power supply 122. The inductive power supply 122 generates an electromagnetic wave 124 directed towards the marker 116. The marker 116 includes a coil, or similar receiver, capable of converting the electromagnetic wave 124 to electric energy to power the marker 116 and/or the marker localization transceiver 118. The electromagnetic wave 124 may also be utilized as a trigger to activate or control the marker 116 and/or the marker localization transceiver 118. For example, receiving the electromagnetic wave 124 by the marker localization transceiver 118 may trigger the marker localization transceiver 118 to send the signal providing localization information for the marker 116. In some examples, the ultrasonic sound waves may trigger or activate the marker localization transceiver 118. In such examples, the inductive power supply may not be necessary, and the marker localization transceiver 118 may be powered by the ultrasonic sound waves by converting the physical energy of the sound waves into electrical energy. In another example, a battery may also be used to power the marker localization transceiver 118. In still another example, the inductive power supply 122 may be incorporated into the ultrasound probe 102. In such an example, the electromagnetic wave 124 is emitted from the ultrasound probe 102.

An incision instrument 126 may also be utilized as part of the ultrasound localization system 100. The incision instrument 126 may be any of a cautery tool, a scalpel, or other type of instrument used for making incisions or intended for use within the interior of the patient 112. For example, the incision instrument 126 may also be an internal probe, such as a pH probe or a thermography probe. The incision instrument 126 may include an instrument localization transceiver 128. The instrument localization transceiver 128 is a transceiver that emits a signal providing localization information for the incision instrument 126. The instrument localization transceiver 128 may include a radio frequency identification (RFID) chip or device for sending and receiving information. For instance, the signal emitted by the instrument localization transceiver 128 may be processed to determine the orientation or location of the incision instrument 126. The orientation and location of the instrument localization transceiver 128 may be determined or provided in three-dimensional components, such as Cartesian coordinates or spherical coordinates. The orientation and location of the incision instrument 126 may also be determined or provided relative to other items, such as the marker 116, the ultrasound probe 102, a magnetic direction, a normal to gravity, etc. With the orientation and location of the incision instrument 126, additional information can be generated and provided to the surgeon to assist in guiding the surgeon to a lesion within the patient, as described further below. The instrument localization transceiver 128 may also be powered and/or trigger via the inductive power supply 122 in a similar manner as the marker localization transceiver 118.

In an example, the instrument localization transceiver 128 is located at the tip of the incision instrument 126. An indicator either on a display 110 or on the incision instrument may indicate a distance from the tip of the incision instrument to the marker 116 or to an edge of the lesion 114. Such a determination may be made from an analysis of ultrasound data or information derived from the signals of the marker localization transceiver 118 and the instrument localization transceiver 128, or a combination thereof. In the case where the incision instrument 126 is a cautery tool, the cautery tool may be configured to turn off when the tip of the cautery tool reaches the edge of the lesion 114. The distance between the tip of the incision instrument 126 and the edge of the lesion 114 and/or the marker 116 may also be determined where the instrument localization transceiver 128 is not located in in the tip of the incision instrument 126. For example, where the size and shape of the incision instrument 126 is known, the location of the tip of the incision instrument 126 can be determined from the location and orientation of the instrument localization transceiver 128. In an example, the respective distances may be determined based on the depth of the detected objects and the respective lateral distance between the objects in the ultrasound image. As discussed above, depth to an object may be determined based on the time of flight of the ultrasound waves. The lateral distance between the two objects may be based on the amount of space between the objects in an ultrasound image. For instance, the lateral distance may be determined based on the number of pixels between the two objects in the image. Lateral distance calculations and processes may be programmed into the ultrasound system 100. The lateral distance calculations may also be trained with samples or phantoms having markings with known distances. The lateral distance may then be calculated between any two objects appearing in the ultrasound image. Those having skill in the art will appreciate other processes and considerations for calculating lateral distances in ultrasound images. Once the depth of objects and lateral distances are determined, the distance from one object to the other in two-dimensions or three-dimensions may be determined through the use of trigonometric and/or geometric relationships between the lines used to measure the depth and lateral distances.

Similarly, the location of the edge of a lesion can be determined from the location and orientation of the marker 116. For example, at the time the marker 116 is inserted into the patient, the relative size and shape of the lesion 114 may also be determined. When the marker 116 is inserted, the edge of the lesion 114 may be determined relative to the location and orientation of the marker 116. For instance, the edge of the lesion 114 may be represented as a function of the location and orientation of the marker 116. As such, in some examples, the marker 116 need not be located directly at or on the lesion 114.

Figure 1C:
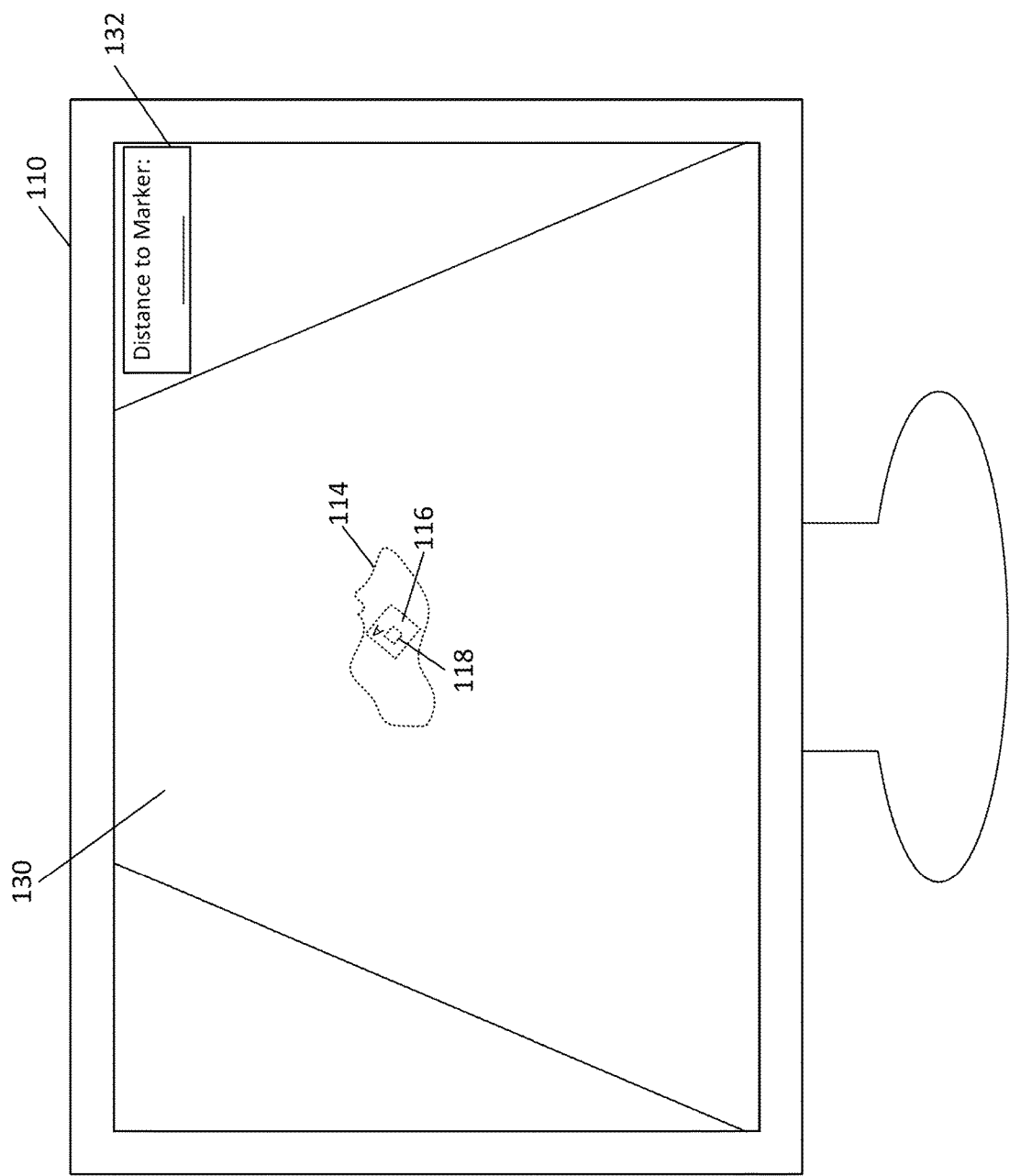
FIG. 1C depicts an example of an ultrasound image including an implanted marker.

FIG. 1C depicts an example of an ultrasound image 130, including an image of the implanted marker 116, on the display 110. The ultrasound image 130 is an example of an ultrasound image where the marker 116 is within the field of view of the ultrasound probe 102. The ultrasound image 130 is generated from image data generated from the detected reflected ultrasonic sound waves 120. Based on the image data or the ultrasound image 130, the marker 116 is identified through the use of image analysis techniques. Because the shape of the marker 116 is not a shape that naturally occurs in the human body, image analysis techniques are able to more easily detect and identify the marker 116 from the image data. For instance, where the marker 116 is in the shape of a cube, the marker 116 stands out as abnormal in ultrasound image data. Alternatively, the marker 116 may be indicated by a user in the ultrasound image 130 once the marker 116 is within the field of view of the ultrasound probe 102.

The image analysis techniques may also be based on machine learning techniques, such as neural networks, deep learning algorithms, statistical analysis techniques, enhanced contrast techniques, or other pattern recognition or matching techniques that are trained based on the shape of the marker 116 implanted in the patient 112. As an example, where the shape of the marker 116 is a cube, the image analysis algorithms may first be trained on a set of ultrasound images containing a cube-shaped marker in different orientations and cross-sectional views. Similar analysis may be achieved by recognizing or quantifying gray scale changes (echogenicity grades) using machine learning. The current ultrasound image 130 or image data is then provided as an input into the trained image analysis algorithms to detect or identify the marker 116. Identifying the marker 116 is generally based on the cross-section of the marker as the ultrasound image 130 is a two-dimensional image with a cross-section of the marker 116. In other aspects, the marker 116 may be a three-dimensional radial-spoke shape, a spherically-shaped lattice structure or a multi-layered spherical structure surrounding a core material, none of which would be naturally occurring in the human body, could be used to differentiate the marker 116 from surrounding anatomy and/or tissue. In this case, the trained set of ultrasound images may comprise different orientations, different grey scale values, and cross-sectional views of the radial-spoke, multi-layered sphere or spherical lattice shapes.

In additional examples, an ultrasound technician or other user may provide additional input to assist in the identification of the marker 116 in the ultrasound image. For example, input may be provided indicating the type of marker 116 that has been implanted in the patient 112. The input may indicate the shape and size of the marker 116. In an example, the input may include providing a model number or other identifying information for the marker 116. Based on the input, the dimensions and other information about the marker 116 may be obtained, such as from a local or remote database storing such information. The dimensions of the marker, or other shape input, may then be used by the image analysis techniques to assist in identification of the marker 116 within the ultrasound image 130. The additional input from the ultrasound technician or other user may also include directly identifying the marker 116 on the ultrasound image 130, such as receiving pointer, touch, or other input to locate the marker 116. For instance, the ultrasound technician may select the marker 116 by clicking on the marker 116 with a mouse on a display of the ultrasound image 130. Distances to the marker 116 may then be based on the input provided by the ultrasound technician. For instance, the distance to the marker 116 may be determined based on the number of pixels in the image between the marker and another point in the image. The input identifying the marker 116 (such as click on the image of the marker 116) may also be utilized in the image analysis techniques to limit the area of the ultrasound image 130 to be analyzed. For example, upon receiving a selection of the marker 116 from an ultrasound technician, a predetermined area around the selection point may be analyzed to identify the marker 116. In other examples, two-dimensional input (such as box) may be provided by the ultrasound technician to provide a boundary for an area that is to be analyzed by the image analysis techniques to identify the marker 116.

The marker 116 may also be made from a material that makes the marker easier to detect within the ultrasound image 130 or image data. For instance, the material of the marker 116 may be selected to be a material that has a high degree of echogenicity, such as Nitinol. By forming the marker 116 of a material having a high degree of echogenicity, the marker 116 will appear brighter in the resulting ultrasound image as materials with higher degrees of echogenicity have a higher ability to reflect ultrasound waves. The marker 116 may also have several flat like surfaces that may aid in the reflection of the acoustic waves, without blocking the anatomy underneath the marker 116 (which could complicate later follow up). In some examples, incorporating air or other gases into the marker 116 may cause the marker 116 to appear brighter in the ultrasound image 130.

The marker 116 may be constructed to provide additional indicators to assist the surgeon in finding the marker 116. For example, the marker 116 may include fluorescent materials or luminescent materials that emit visible light so the surgeon can see the marker 116 during surgery. In some examples, the marker 116 may include microbubbles that burst due to the ultrasonic sound waves, causing the release of luminescent material. Alternatively, the marker 116 may be include an ultrasound contrasting agent, magnetic resonance imaging (MRI) contrasting agent or air, for instance, within orbs at distal ends of radial spokes. In other examples, the marker 116 may include a rare earth magnetic metal that is activated in response to the ultrasound waves or by remote control. In still other examples, the marker 116 may include a material that is capable of converting the ultrasonic sound wave energy into light in the visible spectrum. The marker 116 may also include a light source that is powered by the inductive power supply 122, a battery, or some other power source. Similarly, the marker 116 may also provide acoustic or haptic output to alert the surgeon to the location of the marker. The marker 116 may include a piezoelectric crystal that is activated by ultrasound waves to produce electricity for powering the marker 116, the various sensors and/or the marker localization transceiver 118. In some aspects, the piezoelectric-powered marker may send location data and/or commands (e.g., via marker localization transceiver 118) to other devices, sensors, transceivers, etc.

In other aspects, marker 116 may be composed of or filled with a molecular agent that, upon activation by the ultrasound waves, may be released to bind to cancer cells of lesion 114 and/or to deliver chemotherapeutic agents to the site of lesion 114. When the molecular agent is detectable using a fluorescence or other probe, the specific contours of a margin of the lesion 114 may be identified. For example, a multi-layered spherical marker may comprise different molecular agents within different layers for activation at different times. Alternatively, different layers of the multi-layered spherical marker may become soluble and may dissolve in response to different conditions, such as changes in pH and/or electrolyte levels (e.g., $Ca^{2+}$). That is, the different layers of a multi-layered spherical marker may be formed of different materials that are reactive under different conditions.

In other examples, the marker 116 may be configured to vibrate, causing the marker 116 to increase in temperature. Alternatively, the marker 116 may be composed of a reactive polymer, which may increasing in temperature in response to changes in pH or electrolyte concentration (e.g., $Ca^{2+}$). In such an example, thermography can be performed to assist in identification of the marker 116. For example, the reactive polymer marker may generate a heat map for detecting specific contours of the margin for lesion 114. A temperature probe may also be used as the incision instrument 126 or in addition to the incision instrument 126 to assist in localization of the marker 116.

Identifying the marker 116 may also include identifying, by a processor through image analysis techniques, a particular cross-section of the marker 116 in order to determine an orientation of the marker 116. For instance, in the ultrasound image 130, the orientation of the marker 116 can be determined from its cross-section because the marker 116 is in a cube shape. If the marker 116 has 360 degree rotational symmetry (such as a sphere shape), such an orientation determination would be more difficult. Other shapes for the marker 116 may also be used that have more complex cross-sections and incomplete 360 degree rotational symmetry, such as for example, cones, star-shapes, pyramids, ovoids, tetrahedrons, tetrahemihexacrons a three-dimensional radial-spoke shape, a spherically-shaped lattice structure or a multi-layered spherical structure surrounding a core material, and other shapes such as those shown in FIGS. 10A-F. In such examples, the more intricate shapes may provide additional orientation information from their respective cross-sections. Considerations should be made, however, to ensure that the selected shape is still distinguishable or identifiable from the remaining anatomy and/or tissues of the interior of the patient 112.

In additional examples, the different faces of the marker 116 may be distinguishable from one another based on sandblasting, patterning, numbering, lettering, or other features that may be able to be distinguished in a resultant ultrasound image. The numbering, patterning, lettering, etc. may be raised, embossed, or made of a different material to cause the markings to be more visible in the ultrasound image 130. For instance, as shown in FIG. 1C, an "A" indicator on the cross-section of the marker 116 can be seen in the ultrasound image 130. Thus, the orientation of the marker 116 may be determined by detecting the indicator "A" in the ultrasound image 130.

If the marker 116 is detected or identified, as is the case with ultrasound image 130, the marker 116 is highlighted or otherwise emphasized in the ultrasound image 130. In some examples, the marker 116 is highlighted with a particular color effect, having its brightness increased, or otherwise causing the marker to be highlighted. The marker 116 may also be outlined with an artificial outline to emphasize the presence of the marker 116. A graphical indicator may also be displayed on top of or proximate the marker 116. For example, an arrow may be displayed in the ultrasound image 130 pointing to the marker 116. The color of the marker 116 may also be changed to further highlight or emphasize the marker 116 from the remainder of the ultrasound image 130. The highlighting or emphasis of the ultrasound may be accomplished by modifying the ultrasound image itself or adding a layer on top of the ultrasound image to achieve the desired highlighting or emphasis of the marker 116. Captured ultrasound images may also be fused with mammographic x-ray images (obtained after marker deployment or follow up), in order to aid in the confirmation of the marker location and shape. The permanent metallic/ceramic materials of the markers have distinct shape, therefore the fusion of ultrasound and x-ray is beneficial to identify the specific marker in lesion of interest, as there could be multiple lesions within one breast.

Other indicators may also be triggered when the marker 116 is identified and in the field of view. For instance, an audible sound, such as a beep, may be emitted when the marker comes within a field view. In some examples, a tone having a varying frequency or intensity may also be emitted based on how close the marker 116 is to the center of the field of view. Lights or other visual indicators may also be displayed when the marker 116 comes into the field of view. Haptics (e.g., a vibrating element) on the ultrasound probe 102 may also be activated when the marker 116 comes into the field of view.

Once the marker 116 has been identified and the distance to the lesion 114 or the marker 116 has been determined, the determined distance is displayed on the display 110. For example, the distance may be displayed in a user interface element 132 on the display 110. Other techniques for displaying or otherwise providing an indication of the determined distance are also possible, such as a dedicated indicator panel (e.g., a seven-segment display or a separate LCD screen) or an audible indicator. In other examples, the distance may be displayed or indicated on the ultrasound probe 102 or the incision instrument 126.

The distance to the marker 116, and the orientation of the marker 116 can then be used to guide the incision instrument 126 to the location of the marker 116 in order to excise the lesion. In one example, the orientation of the marker 116 could indicate to the user the point on which to start the incision. In another example, the distance to the marker 116 can be displayed as a vector on the ultrasound image 130 in order to provide one possible path for the incision instrument 126 to follow to remove the lesion. In another example, the distance to the marker 116 can be combined with the distance information about the incision instrument 126 to show whether the incision instrument 126 is close to the marker 116. In some examples, that distance information of the incision instrument 126 can show whether the incision instrument is deviating from the possible incision path.

Figure 1D:
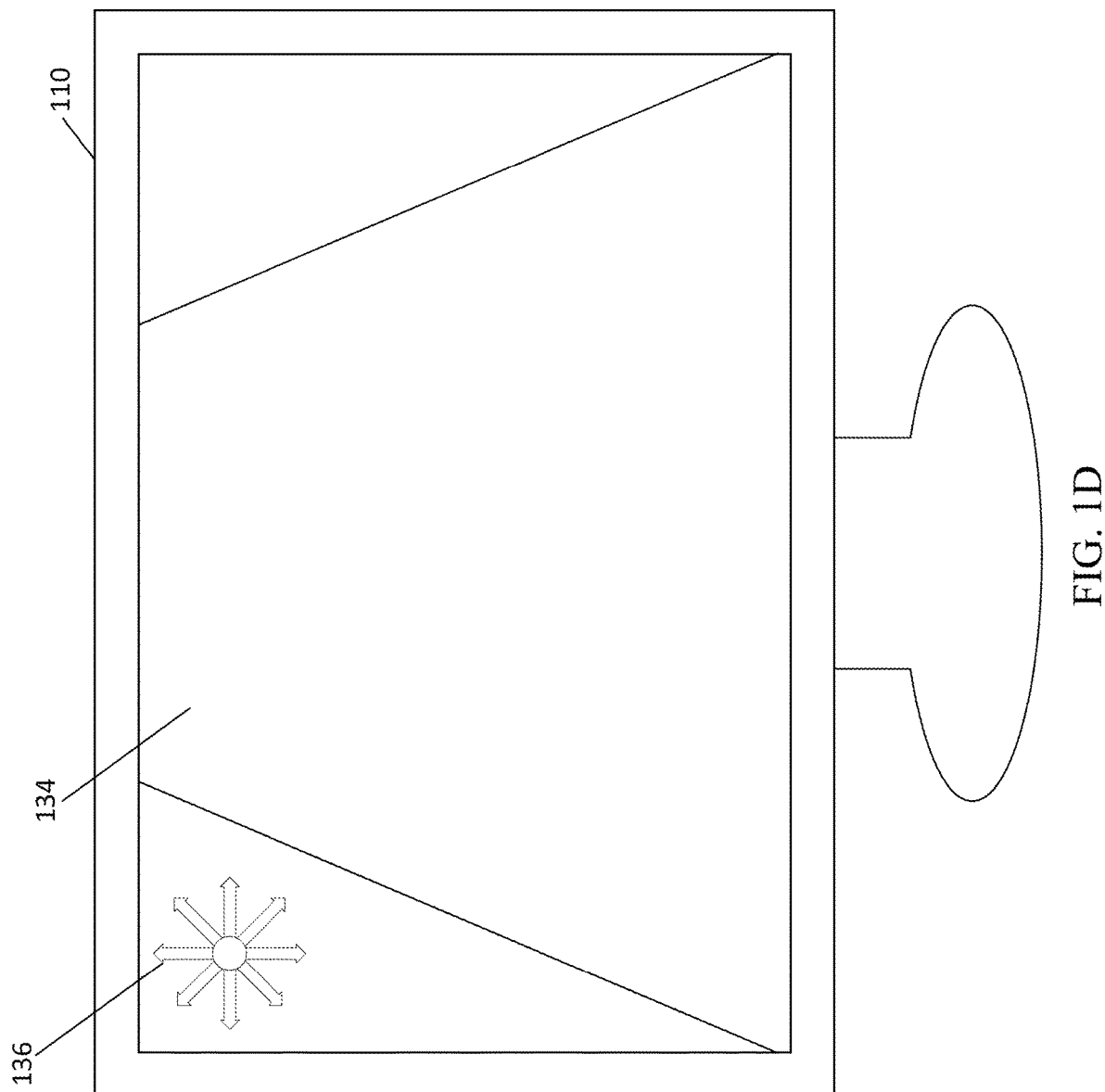
FIG. 1D depicts an example of an ultrasound image not including the implanted marker.

In some cases, the ultrasound probe may be positioned such that the marker 116 is not within the field of view. FIG. 1D depicts an example of an ultrasound image 134 where the marker 116 is not within the field of view. In such an example, an ultrasound technician may be having difficulty locating the marker 116. As such, a navigation indicator 136 may be displayed providing navigation guidance for the ultrasound technician to find the marker 116. From the location and orientation information of the marker 116, based on the ultrasound identification discussed above and/or a signal from the marker localization transceiver 118, the navigation indicator 136 is illuminated to direct the ultrasound technician to the marker 116. In the example depicted, the navigation indicator 136 may include a series of arrows. Individual arrows may be highlighted to direct the ultrasound technician to move the ultrasound probe in a particular direction. For instance, if the marker 116 is out of the field of view and moving the ultrasound probe to the left would cause the marker 116 to come into the field of view, the left arrow is illuminated. While the navigation indicator 136 depicted is in the form of arrows, other types of navigation indicators may be utilized to provide guidance to the ultrasound technician to find the marker 116. For example, different graphical user interface elements may be displayed on the display 110. Other indicators may also be provided in the ultrasound probe 102 itself to assist the technician in find the marker 116 and bringing the marker 116 into the field of view. In examples where the ultrasound probe 102 is automatically controlled and guided, such as by a robotic arm, the location of the marker 116 may be used to automatically guide the ultrasound probe 102 to bring the marker 116 into the field of view.

Figure 1E:
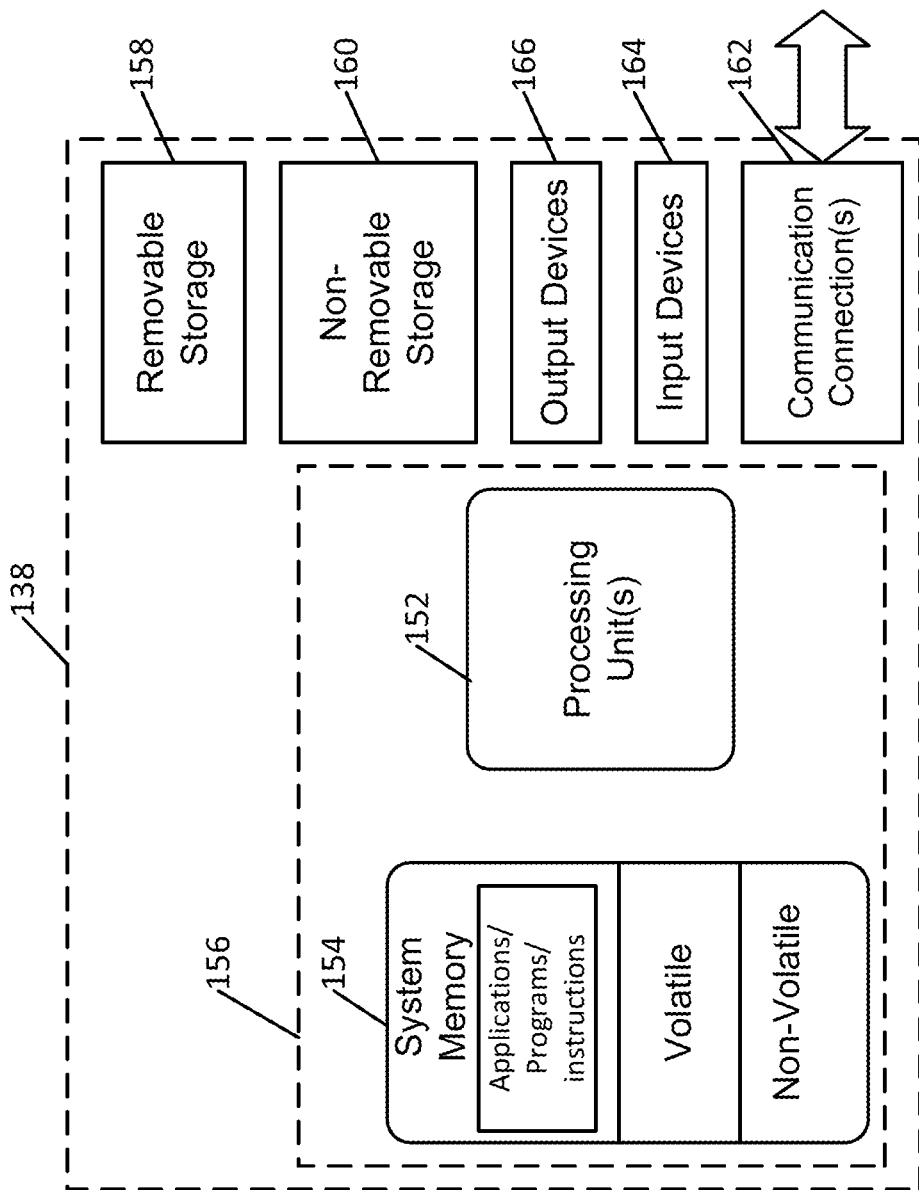
FIG. 1E depicts an example of a suitable operating environment for incorporation into the ultrasound localization system.

FIG. 1E depicts an example of a suitable operating environment 150 for incorporation into the ultrasound localization system. In its most basic configuration, operating environment 150 typically includes at least one processing unit 152 and memory 154. Depending on the exact configuration and type of computing device, memory 154 (storing instructions to perform the active monitoring embodiments disclosed herein) may be volatile (such as RAM), non-volatile (such as ROM, flash memory, etc.), or some combination of the two. This most basic configuration is illustrated in FIG. 1E by dashed line 156. Further, environment 150 may also include storage devices (removable 158, and/or non-removable 160) including, but not limited to, magnetic or optical disks or tape. Similarly, environment 150 may also have input device(s) 164 such as keyboard, mouse, pen, voice input, etc. and/or output device(s) 166 such as a display, speakers, printer, etc. The input devices 164 may also include one or more antennas to detect signals emitted from the various transceivers in the ultrasound localization system 100, such as the probe localization transceiver 108, the marker localization transceiver 118, and/or the instrument localization transceiver 128. Also included in the environment may be one or more communication connections 162, such as LAN, WAN, point to point, etc. In embodiments, the connections may be operable to facility point-to-point communications, connection-oriented communications, connectionless communications, etc.

Operating environment 150 typically includes at least some form of computer readable media. Computer readable media can be any available media that can be accessed by processing unit 152 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 150 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media.

Figure 2A:
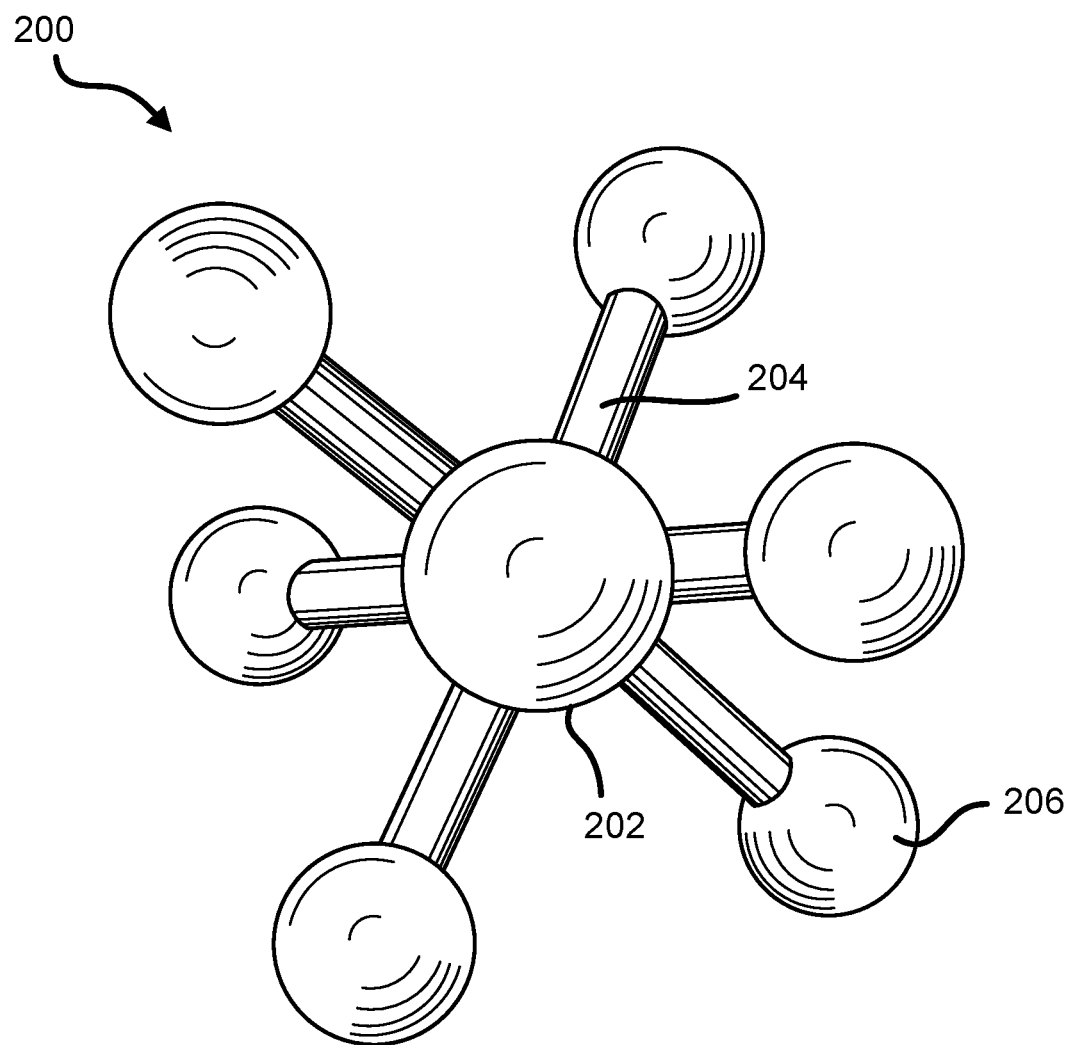
FIGS. 2A-2D depict an example biopsy site marker configured in a condensed and expanded three-dimensional radial-spoke shape.
Figure 2B:
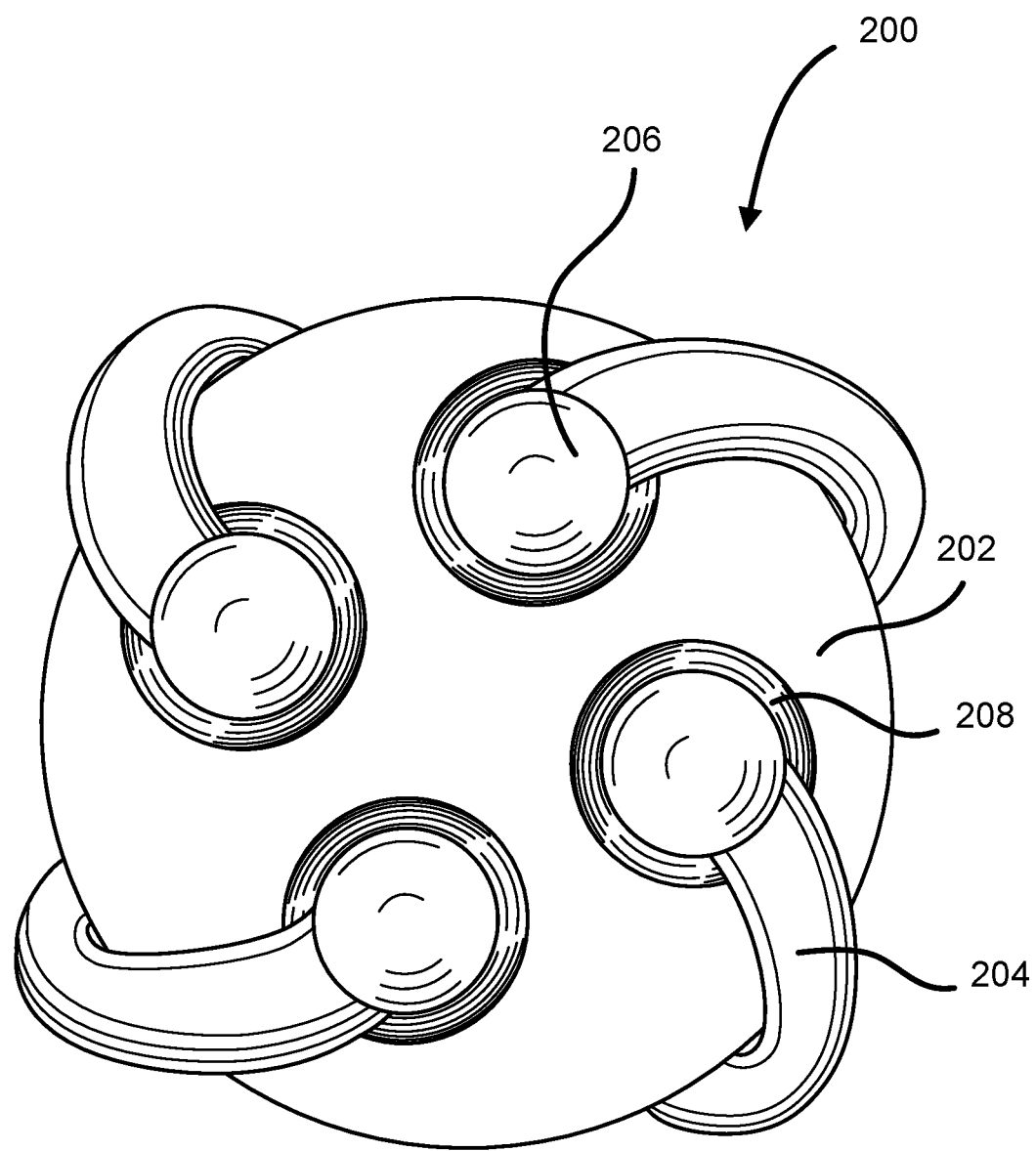

FIG. 2A depicts an example biopsy site marker configured in a three-dimensional radial-spoke shape. As illustrated by FIG. 2A, in an expanded configuration, the radial-spoke marker 200 may comprise a central orb 202 from which a plurality of radial spokes 204 protrude. In aspects, the radial spokes 204 may be orthogonal to one another within three-dimensional space, e.g., the spokes may radiate from the central orb 202 along x, y, and z axes. In other examples, the radial spokes 204 may be located at different angles from the central orb 202 and each other. Each radial spoke 204 may be connected to the central orb 202 at a proximal end and may be connected to a distal orb 206 at a distal end. Any number of radial spoke 204 and distal orbs 206 are contemplated. In one example, the central orb 202 may be hollow, in other examples it can be solid, filled volume. In a condensed configuration shown in FIG. 2B, the radial spokes 204 may fold around or about the central orb 202 such that the radial spokes 204 are substantially laterally aligned with a surface of the central orb 202. In one example, the central orb 202 may have indents 208 to receive the distal orbs 206 in the surface of the central orb 202. For example, in its condensed configuration, the radial spoke marker 200 may be sized for delivery via an elongated needle as part of a marker deployment device. Following insertion at the biopsy site, the radial-spoke marker 200 may deploy into the expanded configuration. Deployment into the expanded configuration may occur in response to removal of the mechanical force that keeps the distal orbs condensed in place, fluid present in patient 112, in response to the body temperature of the patient 112, or otherwise.

For example, the radial-spoke marker 200 may be formed of Nitinol, which may be configured into a first shape (e.g., the expanded configuration) under heated conditions and configured into a second shape (e.g., the folded or condensed configuration) under cooled conditions. Although the radial-spoke marker 200 may be delivered in the condensed configuration, it may "remember" the first shape and automatically deploy into the expanded configuration based at least in part on the shape-memory properties of Nitinol. In one example, the radial-spoke marker 200 may be comprised of a plurality of wires. The distal orbs 206 may be a solid shape or a shape containing openings and also be made of the Nitinol material or made of different materials visible under ultrasound or other imaging modalities such as bio-compatible titanium, polymers, gold, or stainless steel or other materials. In one example, the ends of the plurality of wires can fit inside the distal orbs 206 that would hold them in place. Alternatively, the distal orbs 206 may be attached to the radial spokes 204. Each or some of the distal orbs 206 can be made of different materials than other distal orbs 206.

In additional or alternative aspects, the radial-spoke marker 200 may be delivered in different sizes depending upon an initial (or baseline) size of the targeted lesion. In this way, a progression or regression of the lesion may be detected based on the size of the marker as compared to the size of the lesion at the time of a surgical or other procedure performed under ultrasound.

In some aspects, the lengths of the radial spokes 204 may be equal. In other examples, the length of the radial spokes 204 may comprise different lengths as shown in FIG. 2C. The different lengths of the radial spokes 204 (e.g., radial spokes 204A and 204B) may indicate to the ultrasound system 100, the orientation of the marker 200. As the cross section (or the two-dimensional image) of the marker may vary. In some aspects, the distal orbs 206 may comprise the same size. In other example, the distal orbs 206 may comprise different sizes and may similarly indicate orientation of the marker 200. In at least one embodiment, each or some of the distal orbs can be patterned for example indents of different sizes can increase visibility under some imaging modalities.

Figure 2D:
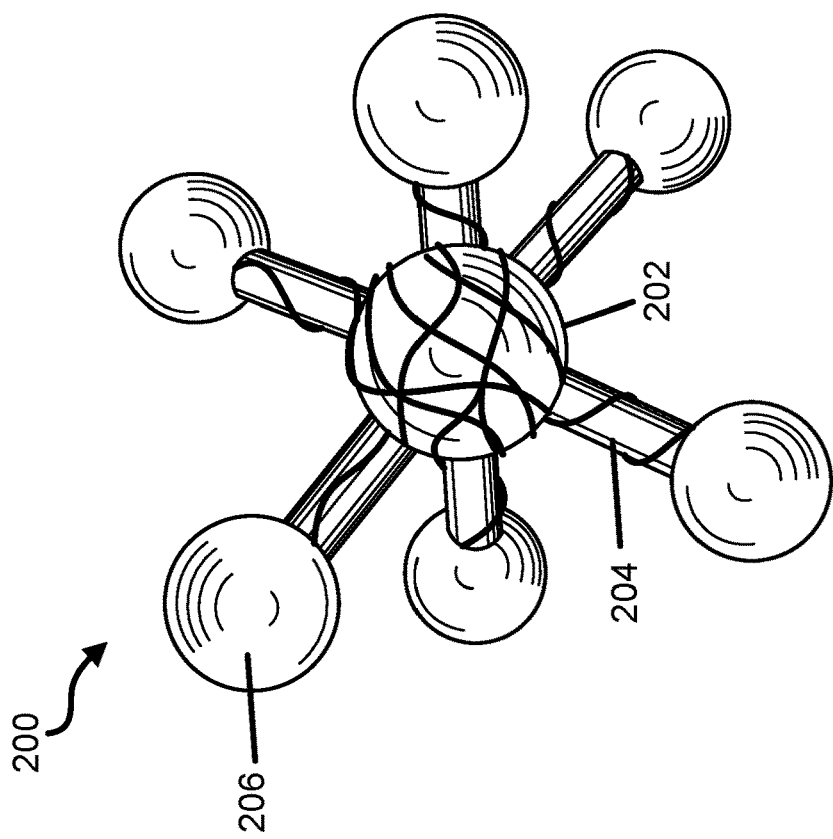
Figure 2C:
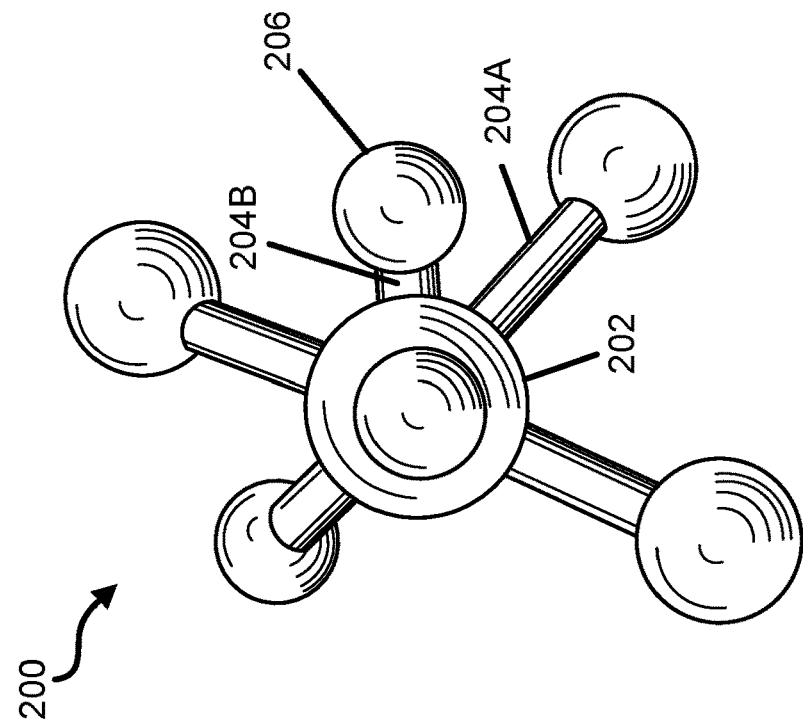

In some aspects, as illustrated by FIG. 2D, the central orb 202 can be made of bio-absorbable material for example, hydrogel, blend and/or copolymer of polyglycolide or polyglycolic acid. In this example the central orb 202 over time may be absorbed by the body, while the distal spheres, not comprising bio-absorbable material remain in the body.

In some aspects, one or more of the distal orbs 206 may be comprised of or encompass a different material. For example, one or more distal orbs 206 may comprise an MRI or ultrasound contrasting agent. Upon activation by ultrasound waves or magnetic resonance, the distal orbs may burst or otherwise release the contrasting agent. In this way, radial-spoke marker 200 may be co-registered within an ultrasound and an MRI imaging modality. In other aspects, the radial-spoke marker 200 may be formed of Nitinol, or some other reflective material which could be a shape memory polymer, which is discernable using ultrasonic imaging technologies. In still other examples, one or more distal orbs 206 may comprise a chemotherapeutic drug that is released to the site of a lesion upon activation by ultrasound waves and/or MRI, or in response to some other condition such as a change in temperature, change in pH, change in electrolyte concentration, etc. In further examples, various distal orbs 206 may react differently to an amount of radiation or chemotherapy delivered to the site of a lesion. In this way, the amount of treatment delivered to the lesion may be detected by radial-spoke marker 200. In some cases, one or more distal orbs 206 may comprise a cancer-cell binding agent that may be released in response to ultrasound waves and/or changes in conditions, as described above. Such cancer-cell binding agent may have properties capable of imaging to enable mapping of the specific margins of a lesion, e.g., via fluoroscopy or some other imaging procedure.

When used as a localization marker during a surgical procedure, ultrasound images of the radial-spoke marker 200 may be generated as a plurality of cross-sectional, two-dimensional views, e.g., on a display 110. Identification of a location of the radial-spoke marker 200, as well as its relative orientation, within the patient may be based on a trained set of ultrasound images of radial-spoke markers in different orientations and cross-sectional views. In this way, the radial-spoke marker 200, which may be inserted with minimal intervention many days or weeks prior to a surgical procedure, may improve patient comfort and reduce challenges in surgical scheduling.

As should be appreciated, radial-spoke marker 200 is not limited to the particular dimensions, materials, configurations and properties described above.

Figure 3:
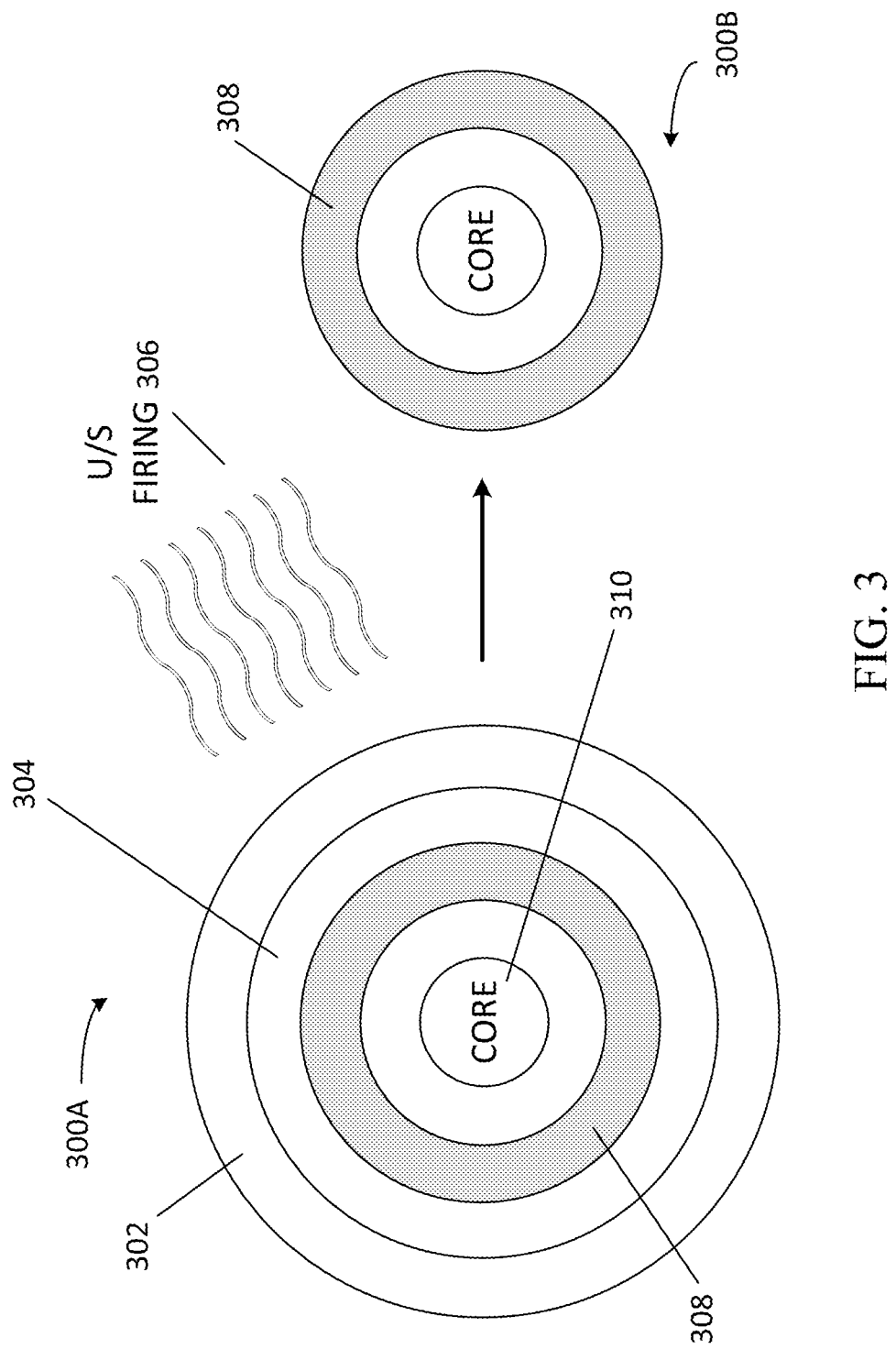
FIG. 3 depicts an example biopsy site marker configured in a multi-layered spherical shape.

FIG. 3 depicts an example biopsy site marker configured in a multi-layered spherical shape. As detailed above, current diagnosis and treatment for breast cancer patients involve several steps. Initially, mammography or other forms of advance imaging may be used to determine whether there are any abnormalities within a patient's breast (s). If so, an outpatient biopsy using image guidance is conducted to retrieve specimens of the site. During the biopsy procedure, a permanent implant (e.g., biopsy site marker) may be deployed to 'mark' the lesion that was biopsied. This permanent marker allows a physician to follow up, and possibly a surgeon to resect (surgically remove) the tumor. Traditionally, a radiologist is needed prior to surgical removal to image the breast using mammography and to place a wire in perpendicular orientation to the marker location. This wire remains in the patient throughout that day until the surgery, at which time the surgeon follows the metal wire and excises the marker and the lesion in an open surgery.

Following surgery, oral systemic chemotherapy may be delivered in order to reduce any margins or lymph nodes where the cancer could have spread. Due to the sometimes harsh and systemic nature of the drugs, emphasis has been moving toward targeted drug delivery to the lesion site. However, current marking technologies are limited due to the materials used, marker shape, size and ultimate detectability when visualized under advanced imaging (X-ray, MRI, ultrasound). Additionally, current commercial markers are passive landmarks and do not collect or transmit data, nor are they able to respond to external stimuli. Further limitations include, for example, the lack of marker distinctiveness that prevents distinguishing markers from anatomical features and scarred tissue, as well as poor imaging characteristics of marker fabrication materials. Use of ultrasound as an imaging technology offers several benefits, including no radiation and low cost, ease of use, and broad availability of technicians and machinery. Not only so, but ultrasound imaging provides a better image of the lesion, lesion margin appearance and surrounding tissues. However, finding a marker under ultrasound can be cumbersome. Metal markers tend to be very small and show up hyperechoic under ultrasound, causing them to be confused with natural features (e.g., such as air bubbles, calcifications, cooper ligaments, etc.). While the crystallinity of these polymers (e.g., PLA, PGA, etc.) can be easily identified when compared to natural breast tissue, most polymer markers are resorbable and do not last very long in vivo. The shape of some polymer markers presents as a long strand of 'rice-like' bodies and may be confused with Cooper ligaments. Hydrogel polymers, on the other hand, can be easily identified due to their water content, which is distinct and hypoechoic in nature (once fully hydrated), but have the limitation of degradation and potential scar formation, which may appear malignant. Also, the appearance of the hydrated hydrogel could appear like a cyst or fibroadenoma (wider and shorter) with clear margins, there should be an internal feature that could aid in the differentiation from naturally occurring benign lesions. Ceramic materials may also be used for markers, but due to their crystallinity, and hard nature, they appear hyperechoic and tend to be very small in size and do not have capability to change size or shape.

In sum, radiologists and surgeons would benefit if biopsy site markers could be used as localization markers during surgery. Ultrasound-detectible markers may satisfy this currently-unmet need as highly ergonomic, low cost, no radiation, readily available, non-invasive and patient friendly solutions. Similarly, providing surgeons with a 'wire-free' option in which they could localize intraoperatively the marker and the lesion, would enable easier access and better surgical planes, leading to better surgical and cosmetic outcomes.

A multi-layered marker may comprise a central core 310 enveloped by concentric layers of one or more different materials. For example, the multi-layered marker 300 may be a multi-layered composite construct, made of biocompatible non-inflammatory polymers (could be synthetic or animal derived) with the central core 310 of a permanent material (non-biodegradable, such as metal or ceramic, or a non-degradable polymer such as nylon, PMMA, PEEK, PVP, PVA, etc.). The outer layers of the multi-layer construct may have a scaffold-like appearance with a series of open and closed pores. The closed pores may be filled with air, saline, or a drug. These liquid- or gas-filled pores would serve as a vehicle to aid in localization of the multi-layered marker within the breast tissue. The multi-layer construct may also be composed of a series of biodegradable polymer layers (e.g., 1-500 nm in thickness), with different material properties than the scaffold layers or the central core, which may be deposited using a variety of thin film assembly techniques. In aspects, each layer could contain a different percentage of porosity (e.g., closed pores filled with liquid or gas). This construct surrounds the permanent core material. The multi-layered marker 300 may be delivered minimally invasively during a biopsy procedure using image guidance. The radiopaque permanent element (e.g., central core 310) would be clearly distinguishable using X-ray, while the polymeric layers could be visualized under Ultrasound and/or MRI.

In aspects, the multi-layered marker 300 may remain in the patient's breast at the location of the biopsy site and will provide clear margins and shape under ultrasound, with no posterior acoustic shadowing. If the results of the biopsy are positive, at a follow up appointment, the surgeon uses an ultrasound linear transducer (e.g., about 7-14 MHz) and places it on the breast. As soon as the surgeon starts scanning, the multi-layered marker 300 would be visible. That is, once the surgeon places the probe on the target for a few seconds (scanning back and forth), the internal content of the pores within the marker composite will resonate, creating a detectable nonlinear echo response to the ultrasound. Due to the content of the pores (e.g., gas or liquid), when the ultrasound acoustic waves hit the marker, the waves are not able to continue and bounce back. Moreover, the micro-sized acoustic response may cause layers to break or shed off of the outer layers. Such response would be seen by the user as 'scattering' as the original acoustic waves are redirected due to the presence of rough surfaces (as layers breaks off), which would be easily discernable from natural tissue and anatomy by the user. In this way, the user would be able to localize the multi-layered marker 300, including its depth and location.

Due to the nature of the multi-layered marker 300, multiple types of polymers may be deposited with different lengths of degradation (e.g., from six months to one year or more). In this way, the multi-layered marker 300 would not be affected by the natural degradation and inflammatory response of the body to a foreign object. Also, as the different layers can make a distinct echogenic profile, the marker can be easily distinguished when each layer breaks off. Thus, the multi-layered marker 300 solves a critical need, which is the localization of the marker/biopsy site from three to six months after biopsy. For example, these multiple layers of different thicknesses could be shed off every time there is a follow up ultrasound scan, to aid in visualization. This is a critical time period, as most chemotherapy regimens last between three to six months. During this period, it would now be possible to gauge how well the chemotherapy is working based ultrasound evaluation of the lesion site based on the marker. The fact the multi-layered marker 300 is easily seen under ultrasound provides flexibility for the surgeon to localize the lesion without additional equipment (or help from advanced imagers), either intraoperatively in the operating room (OR).

The multi-layered marker 300 could also be used for targeted drug delivery, as each layer could serve as a personalized cocktail of chemotherapy drugs that could be released remotely and precisely. In other aspects, the multi-layered marker 300 could be activated for localization using a remote activation. For instance, the permanent core could be fabricated of a rare earth magnetic metal coated with layers of polymers. For later localization and activation, an external strong magnet probe could be placed on the breast. When placed close to the marker, rare earth magnetic metal may extend its 'length' or change its shape due to the magnetic field, causing the external polymer layers to either break off or move elastically with the core. Such 'movement' within the marker can be easily seen under ultrasound. However, use of such magnetic metal materials would prevent the patient from being a candidate for MRI.

Although multi-layered markers 300A, 300B are illustrated as spheres, a multi-layered marker may be provided in any suitable shape or size. For example, the multi-layered marker may be in the shape of a square or any other geometric shape. In aspects, one or more layers of the multi-layered marker may be composed of or comprise a chemotherapeutic drug. Alternatively, one or more layers may be composed of or comprise a cancer-cell binding agent. For example, firing ultrasound waves 306 may cause one or more layers (e.g., first layer 302 and/or second layer 304) of the multi-layered marker 300A to dissolve or break off, as illustrated by multi-layered marker 300B in which third layer 308 is now an outer layer. When first layer 302 and/or second layer 304 are composed of a chemotherapeutic drug, treatment may be delivered directly to a lesion in response to ultrasound waves. When first layer 302 and/or second layer 304 are composed of a cancer-cell binding agent exhibiting properties capable of detection by different imaging modalities, a specific margin or boundary of a lesion may be identified (e.g., via fluoroscopy or other imaging technique). In some aspects, first layer 302 and second layer 304 may exhibit different properties such that the chemotherapeutic drug and/or cancer-cell binding agent is released at different times or under different conditions. In other aspects, one layer may comprise a chemotherapeutic drug while another layer may comprise a cancer-cell binding agent, which layers may be activated at different times or under different conditions.

Alternatively, first layer 302, or another layer such as second layer 304 or third layer 308, may be composed of a material that is reactive to changes in pH, temperature, electrolyte concentration, or other condition of a bio-environment. For example, in response to changes in conditions, the material may fluoresce, become soluble and dissolve, exhibit changes in echogenicity, release a contrasting agent, or the like. Tumor growth or progression may be evidenced by a reduction in pH (e.g., increased acidity), an increase in temperature (e.g., due to increased cellular metabolism and/or vascularization), and/or a decrease in free calcium ions (e.g., due to an increase in $Ca^{2+}$ uptake by cancer cells) in surrounding tissues. In this case, a material that is reactive to changes in pH, temperature and/or electrolyte concentration may provide an in-situ indication of a progression or regression of a lesion.

In still other examples, one or more layers of the multi-layered marker 300A and/or 300B may comprise or be composed of a rare earth magnetic metal, which may be activated by ultrasound waves or an external remote control. For example, the rare earth magnetic metal may lengthen or shorten in response to activation. In this way, a shape of the multi-layered marker 300A and/or 300B may be altered upon activation of the rare earth magnetic metal. For instance, based on a change in shape, a multi-layered marker may be more readily detectable as a localization marker under ultrasound during a surgical procedure.

As should be appreciated, multi-layered marker 300A and/or 300B are not limited to the particular dimensions, materials, configurations and properties described above.

Figure 4A:
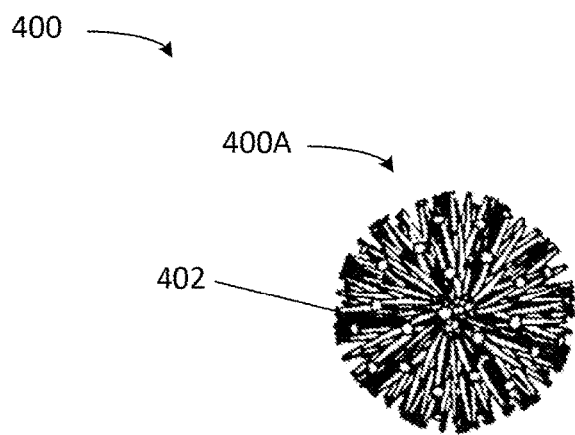
FIGS. 4A-4C depict an example biopsy site marker configured in an expandable spherical lattice structure.
Figure 4B:
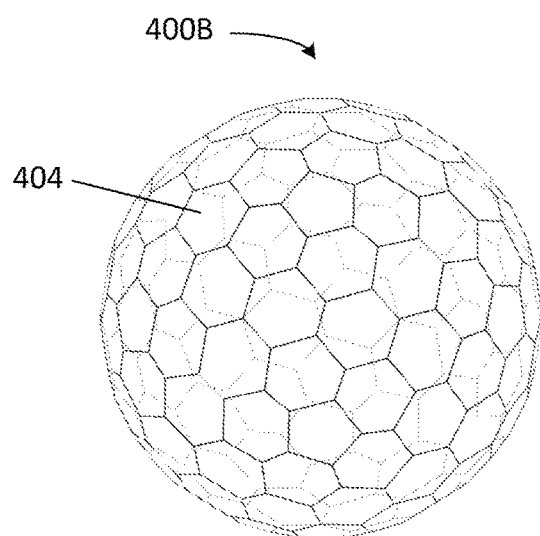
Figure 4C:
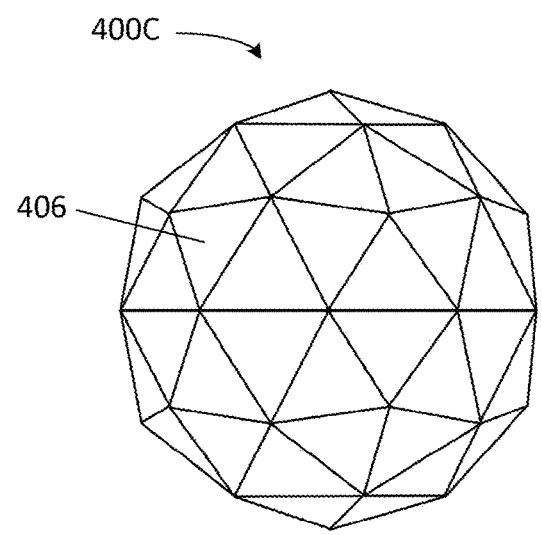

FIGS. 4A-4C depict an example biopsy site marker configured in an expandable spherical lattice structure. Spherical lattice marker 400 may be formed of Nitinol wire or some other shape-memory alloy or polymer. The Nitinol wire may be formed into a geodesic cage. In examples, the Nitinol wire may form a two-dimensional geometric shape (e.g., pentagon, triangle, etc.) on facets or faces on the surface of the geodesic cage, e.g., pentagon facet 404 or triangle facet 406. In its condensed state (e.g., spherical lattice marker 400A), the wire edges of the geometric facets may fold inward to create spikes 402. In some cases, the Nitinol wire may be configured into a first shape (e.g., an expanded configuration) under heated conditions and configured into a second shape (e.g., a folded or condensed configuration) under cooled conditions. Although the spherical lattice marker 400 may be delivered in the condensed configuration (e.g., second shape), it may "remember" the first shape and automatically deploy into the expanded configuration (e.g., spherical lattice marker 400B, 400C) based at least in part on the shape-memory properties of Nitinol. Alternatively, the spherical lattice marker 400 may be configured with a wire or other actuator for "pulling" the spherical lattice marker 400 from a condensed state into an expanded state after insertion at the biopsy site.

In some cases, the spherical lattice marker 400 may be delivered in various sizes depending on a size of a target lesion. In this way, a progression or regression of the lesion may be detected based on the size of the marker as compared to the size of the lesion at the time of a surgical or other procedure performed under ultrasound. When used as a localization marker during a surgical procedure, ultrasound images of the spherical lattice marker 400 may be generated as a plurality of cross-sectional, two-dimensional views, e.g., on a display 110. Identification of a location of the spherical lattice marker 400, as well as its relative orientation, within the patient may be based on a trained set of ultrasound images of spherical lattice markers having the same geometric facets in different orientations and cross-sectional views. In this way, the spherical lattice marker 400, which may be inserted with minimal intervention many days or weeks prior to a surgical procedure, may improve patient comfort and reduce challenges in surgical scheduling.

As should be appreciated, spherical lattice markers 400A-C are not limited to the particular dimensions, materials, configurations and properties described above.

Figure 5:
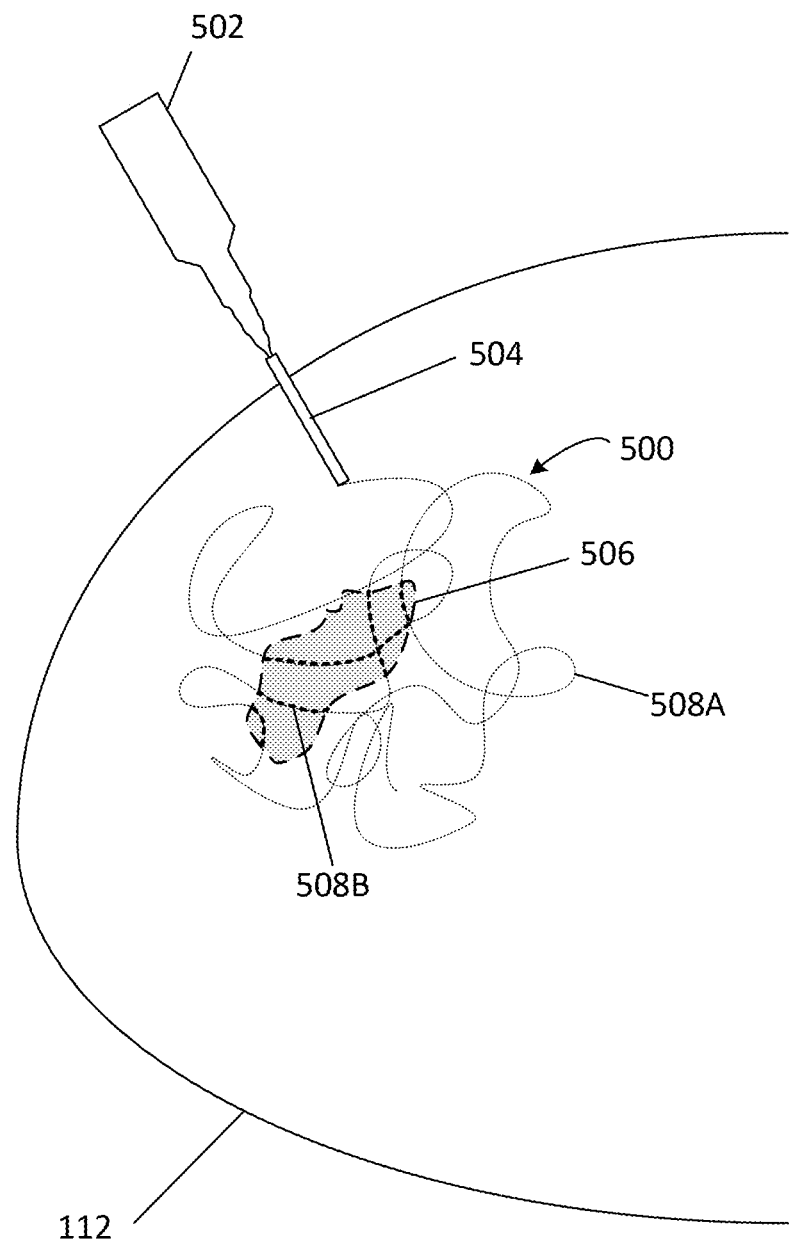
FIG. 5 depicts an example biopsy site marker configured as a fibrous polymer.

FIG. 5 depicts an example biopsy site marker configured as a fibrous polymer. Fibrous polymer marker 500 may be injected into a biopsy site following a biopsy procedure of a patient 112. In aspects, the fibrous polymer marker 500 may be injected using an injection device 502 through a hollow tube or conduit 504 into tissues surrounding a lesion 506. In some aspects, hollow tube 504 may be biodegradable and reabsorbed by patient 112. For example, at the time of a biopsy, the resorbable tube 504 could be placed after a core is removed, or could be pushed out from the distal end of the introducer at the site. The resorbable tube 504 (e.g., about 2 cm in length) may remain at the biopsy site as a 'place holder' and can be localized using ultrasound (as a distinct flat hyperechoic structure, with a hollow hypoechoic core). Furthermore, the resorbable tube 504 may now serve as an introducer for delivering a 'sensing' fiber (e.g., suitable for fibrous polymer marker 500), which may be less than about 1 millimeter in diameter. Such sensing fiber can be used by the surgeon and/or a radiologist to minimally invasively map out the biopsy site region. In this way, the sensing fiber may serve as a guiding system, which may shoot light or sound waves into the biopsy cavity (e.g., where the biopsy core was removed), and it can capture the response from the surrounding tissue. For example, cancerous areas within the cavity wall may have different hardness or other properties that reflect or absorb the emitted waves in different ways than normal tissue. The cancerous area can then act as a beacon, as hard cancerous areas have been known to have distinct elastic moduli (e.g., as determined by elastography). In some cases, the sensing fiber may be connected to a computing system with a user interface for illustrating a 'heat' map of the entire cavity as they fluoresce under a specific wavelength. An additional user interface could help with imaging the 'hot spots' and could co-register or fuse with previous ultrasound images of FIG. 1C. This system could be used to minimally invasively map out the cavity, and to confirm there are no remaining cancerous areas. The user interface could be co-registered with other imaging modalities (such as ultrasound or MRI), enabling the surgeon to understand where the 'hot spots' are relative to anatomical features. The sensing fiber could also be a vehicle for delivering drugs to the location of the lesion at the biopsy site. If light is used, then prior to inserting the fiber, the surgeon could inject a liquid agent designed to bind to specific cancerous 'biomarkers' or cells. Thereafter, these spots could be visualized using near infrared (NIR) or fluorescence principles. In this case, a higher concentration of spots would imply that there is a cancer left behind. In some cases, after resection, a similar resorbable tube could be placed. In this case, if there is a need for additional surgery (e.g., for cosmetic outcomes, implants, or addressing remaining margins), a surgeon could use the post-resection resorbable tube to map out remaining tissues and/or margins before performing the additional procedures.

The benefits of using a resorbable tube and/or sensing fiber may be far-reaching. For example, current intraoperative solutions use excised ex vivo tissue for imaging using different technologies, such as X-ray (which doesn't provide clear margins), OCT medical imaging, Raman Spectroscopy, Ultrasound, etc. However, all of these imaging modalities evaluate excised tissue outside of the body, so there are no (or very limited) current in situ intraoperative solutions to detect remaining margins within the cavity. Rather, surgeons must artificially evaluate and understand where the margins could be, as well as any additional tissue that should be retrieved. Thus, benefits of the sensing fiber include minimally invasively delivery, e.g., after biopsy or resection, and in situ imaging, which could ultimately alter the way surgeries are planned and carried out. The fiber placed in situ could overcome issues with current external NIR probes that can only detect 'targets' within a depth of less than a couple of centimeters due to optical scattering across heterogeneous tissue planes.

In aspects, the fibrous polymer marker 500 may be comprised of any suitable sensory fiber that is biocompatible and remains substantially stable (e.g., insoluble) for a period of time within patient 112. Sensory fibers may include fibrous polymers that are reactive to light, heat, ultrasound waves, changes in pH, changes in electrolyte concentration, and the like. For instance, fibrous marker 500 may detect an increase in temperature, e.g., due to increased cellular metabolism and/or increased vascularization, which may be indicative of a progression of lesion 506. In contrast, fibrous polymer marker 500 may detect a decrease in temperature, which may be indicative of a regression of lesion 506. In another example, fibrous marker 500 may detect a decrease in pH and/or free calcium ion concentration in the vicinity of lesion 506, which may be indicative of a progression of lesion 506. Conversely, an increase in pH and/or free calcium ion concentration may be indicative of a regression of lesion 506.

In response to detecting light, ultrasound waves, changes in temperature, changes in pH, changes in electrolyte concentration, and the like, the structure or properties of the fibrous polymer marker 500 may be altered. For instance, portions of fibrous polymer marker 500 that detect such conditions may fluoresce, thicken, emit visible light, emit heat, crystalize, increase echogenicity, or otherwise be altered in structure or properties, as illustrated by altered fibrous material 508B. In contrast, other portions of fibrous polymer marker 500 that do not detect such conditions may remain unaltered, as illustrated by unaltered fibrous material 508A. When the altered fibrous material emits heat in response to detecting changes in the micro-environment surrounding lesion 506, infrared thermography (IRT) or thermal imaging may be used to visualize a heat map produced by the altered fibrous material in the vicinity of lesion 506. In this way, changes in the margin of lesion 506 may be mapped or outlined, new masses may be identified, changes in the bio-environment (e.g., changes in pH, temperature, or electrolyte concentration) surrounding the lesion 506 may be detected, and the like. Similarly, other imaging techniques may be utilized to detect other alterations of the fibrous material, e.g., ultrasonic imaging, magnetic resonance imaging, etc. Suitable sensory fibers may include but are not limited to: aramid fiber, aramid-polymethylmethacrylate (aramid-PMMA), high modulus carbon fiber, hydrogel-based optical fiber, fiberglass, and the like.

As should be appreciated, fibrous polymer marker 500 is not limited to the particular dimensions, materials, configurations and properties described above.

Figure 6:
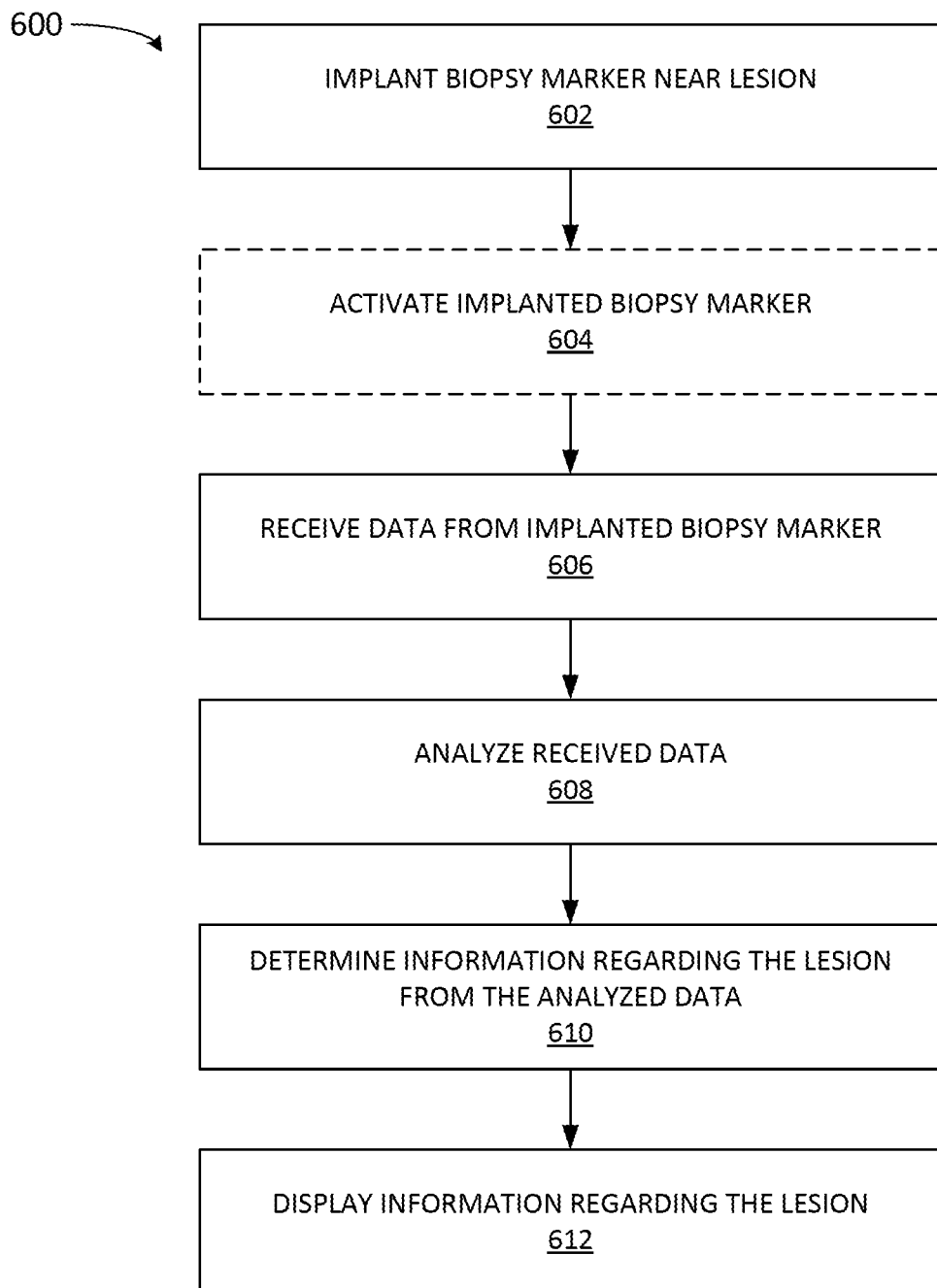
FIG. 6 depicts an example method for determining information regarding a lesion from an implanted marker.

FIG. 6 depicts an example method 600 for determining information regarding a lesion from an implanted marker. The operations of method 600 and the other methods discussed herein may be performed by at least one processor in conjunction with other components of a suitable operating environment, such as the operating environment 150 in FIG. 1E, within a system such as system 100 depicted in FIGS. 1A-1D.

As detailed above, a biopsy site marker may be implanted at or near a lesion prior to a surgical procedure. For instance, at operation 602, e.g., during a biopsy procedure, the biopsy site marker may be implanted into a patient near a suspicious lesion. As described above, the implanted marker may be configured with special features or properties for delivering drugs or treatments and/or monitoring a progression or regression of the lesion. Moreover, the implanted marker may be detectable as a localization marker during a surgical procedure subsequent to the biopsy procedure. In this way, the implanted marker may not merely serve as a landmark for future examination of the lesion, but may be configured to monitor or treat the lesion as well as serve as a localization marker during a subsequent surgical procedure. Thus, the implanted marker may not only minimize intrusion of the patient, but provide on-going benefits with regard to the treatment, diagnostics and localization of the lesion.

At optional operation 604, the implanted marker may be activated. The implanted marker may be activated in any of a number of ways. For instance, the implanted marker may be activated by ultrasound waves, an ingested agent, or an external remote. Alternatively, the implanted marker may be activated (or reactive) to changes in conditions in a bio-environment of the lesion. For instance, the implanted marker may react or be responsive to changes in pH, changes in temperature, changes in electrolyte concentration, and the like. In response to activation, the structure of the implanted marker may be altered (e.g., by thickening, folding, expanding, dissolving, lengthening or shortening, and the like) or the properties of the implanted marker may be altered (e.g., by emitting heat, emitting visible light, increasing or decreasing echogenicity, vibrating, increasing or decreasing solubility, fluorescing, releasing a drug or agent, and the like). In some cases, in response to activation, the implanted marker may send or receive monitored data (e.g., via a transceiver) to or from an external device.

At operation 606, data may be received from the implanted device. In some cases, the data may be received by performing imaging or some other technique to gather data from the implanted marker. For instance, one or more of ultrasound imaging, MRI, X-ray imaging, thermography, elastography, fluoroscopy, and the like, may be performed to gather data associated with the implanted marker's location, orientation, properties or structure. Alternatively, the implanted marker may actively send data to an external device. For instance, in the case of an implanted chip, the implanted marker may send monitored data regarding the lesion (e.g., such as temperature data, pH data, electrolyte concentration data, blood flow or pressure data, and the like).

At operation 608, the received data may be analyzed. For instance, data gathered by imaging or other technique may be analyzed to detect changes in the structure or properties of the implanted marker, such as size, shape, echogenicity, luminosity or fluorescence, heat, and the like. Based on the composition of the implanted marker, such changes in structure or properties may be indicative of changes in a bio-environment surrounding the implanted marker, such as changes in temperature, pH, electrolyte concentration, etc. Additionally or alternatively, using ultrasound or other imaging modality, a location or orientation of the implanted marker may be determined, as described above with reference to FIGS. 1A-1D. Still further, raw data received from an implanted chip or sensor associated with the implanted marker may be processed and analyzed. When processed, the raw sensor data may provide information regarding a bio-environment surrounding the implanted marker, such as temperature, pH, electrolyte concentration, blood flow, blood pressure, etc.

At operation 610, information regarding the lesion may be determined from the analyzed data. For instance, if the analyzed data is indicative of an increase in temperature in the bio-environment surrounding the implanted marker, it may be determined that the lesion is progressing or growing. Similarly, if the analyzed data is indicative of a decreasing in pH and/or free calcium ion concentration in the bio-environment surrounding the implanted marker, it may be determined that the lesion is progressing or growing. Conversely, if the analyzed data is indicative of a decrease in temperature or an increase in pH and/or free calcium ion concentration, in the bio-environment surrounding the implanted marker, it may be determined that the lesion is regressing or shrinking. Additionally or alternatively, if the analyzed data is indicative of a margin of the lesion (e.g., via ultrasound imaging, thermography, fluoroscopy, etc.), the determined margin may be compared to previous margin information to determine whether the lesion is progressing or regressing. In still other examples, a relative size of the implanted marker may be compared to a size of the lesion (e.g., based on margin data as described above). When a size of the implanted marker is indicative of an initial or baseline size of the lesion, the determined relative size of the implanted marker based on the analyzed data may be used to determine whether the lesion has progressed or regressed. As should be appreciated, additional information regarding the lesion may be determined from analyzing data associated with the implanted marker, as described throughout the present disclosure.

At operation 612, the determined information regarding the lesion may be displayed on a display device. For instance, the determined information may be in the form of a report, one or more images, etc. In some cases, a notification of the determined information may be forwarded to medical personnel and/or the patient.

Figure 7A:
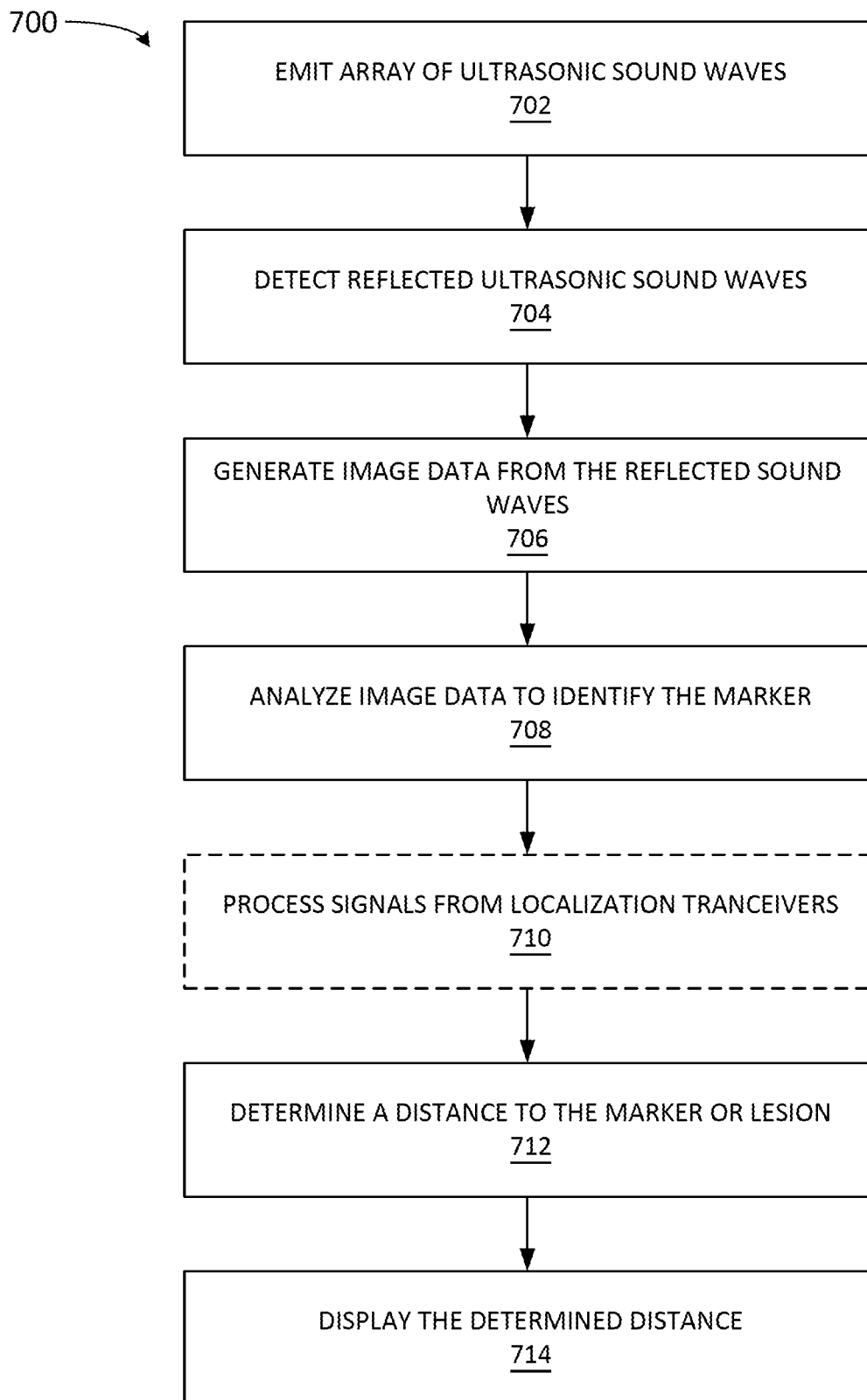
FIG. 7A depicts an example method for localization of a lesion or an implanted marker.

FIG. 7A depicts an example method 700 for localization of a lesion or implanted marker. As detailed above, the marker may have been implanted at or near the lesion prior to a surgical procedure. For instance, when the lesion was detected in a patent, the marker may have been implanted during a biopsy procedure. In this way, rather than requiring coordination and placement of a localization wire at the time of surgery, the previously-implanted marker may be utilized to localize the lesion during the surgical procedure. Thus, logistics and scheduling on the day of surgery are simplified, as well as reducing an overall surgical time for the patient. Further benefits are realized because the implanted marker may be specially designed for detection using ultrasound or other imaging technologies to provide live imaging and lesion location data during the surgical procedure. The operations of method 700 and the other methods discussed herein may be performed by at least one processor in conjunction with other components of a suitable operating environment, such as the operating environment 150 in FIG. 1E, within a system such as system 100 depicted in FIGS. 1A-1B.

At operation 702 an array of ultrasonic sound waves are emitted from an ultrasonic transducer of an ultrasound probe. The ultrasound waves enter the interior of the patient and are reflected from the components of the interior of the patient, including natural tissue as well as the implanted marker, as discussed above. The reflected ultrasonic waves are then detected at operation 704. At operation 706, ultrasound image data is then generated from the detected reflected ultrasonic sound waves. The ultrasound image data may be B-mode ultrasound imaging data.

At operation 708, the image data is analyzed by a processor of the ultrasound localization system to identify or detect the implanted marker within the image data. As discussed above, the image analysis techniques may be based on image processing techniques, and machine learning techniques, such as neural networks, deep learning algorithms, or other pattern matching techniques, that are trained based on the shape of the marker implanted in the patient. As an example, where the shape of the marker has a unique cross-section in 360 degrees of rotation, the image analysis algorithms may first be trained on a set of ultrasound images containing a cube-shaped marker in different orientations and cross-sectional views. A current ultrasound image or image data is then provided as an input into the trained image analysis algorithms to detect or identify the marker. Identifying the marker may generally be based on the cross-section of the marker as the ultrasound image is a two-dimensional image.

Identifying the marker may also include identifying a particular cross-section of the marker in order to determine an orientation of the marker. For instance, the orientation of the marker can be determined when the marker is detected in at least two different sections based on different viewing angles, such as cube or a rectangular prism. If the marker has symmetry in 360 degrees of rotation, determining an orientation from ultrasound imaging alone is more difficult. In some examples, the marker may be identified by a user, such as an ultrasound technician, on a display of an ultrasound image. Such an identification may be provided as an input into the ultrasound system (e.g, a click of a pointer on the display) to allow for a distance to the marker to be determined. For instance, the distance may be determined based on the number of pixels between the two objects in the image.

If the marker is detected or identified in operation 708, an ultrasound image may be displayed that highlights or otherwise emphasizes the marker. In some examples, the marker is highlighted with a particular color, having its brightness increased, or otherwise causing the marker to be highlighted. The marker may also be outlined with an artificial outline to emphasize the presence of the marker. A graphical indicator may also be displayed on top of or proximate the marker. For example, an arrow may be displayed in the ultrasound image pointing to the marker. The color of the marker may also be changed to further highlight or emphasize the marker from the remainder of the ultrasound image. The highlighting or emphasis of the ultrasound may be accomplished by modifying the ultrasound image itself or adding a layer on top of the ultrasound image to achieve the desired highlighting or emphasis of the marker.

Other indicators may also be triggered when the marker is identified and in the field of view. For instance, an audible sound, such as beep, may be emitted when the marker comes within a field view. In some examples, a tone having a varying frequency or intensity may also be emitted based on how close the marker is to the center of the field of view. Lights of other visual indicators may also be displayed when the marker comes into the field of view. Haptics on the ultrasound probe may also be activated when the marker comes into the field of view.

At optional operation 710, signals from the various localization transceivers are processed by at least one of the processors in the ultrasound localization system. As discussed above, the ultrasound localization system may include at least a probe localization transceiver, a marker localization receiver, and/or an instrument localization transceiver. Those transceivers emit signals providing localization information for the device to which they are attached or incorporated, e.g., the ultrasound probe, the marker, and/or the incision instrument. The signal(s) emitted by the transceiver(s) may be processed to determine the orientation or location of the ultrasound probe, the marker, and/or the incision instrument at operation 712. The orientation may also be determined from the cross-section of the marker and/or the incision instrument in the ultrasound image. The orientation and location of those devices may be determined or provided relative to other items, such as the incision instrument, the marker, the ultrasound probe, a magnetic direction, a normal to gravity, etc. With the orientation and location of the devices, additional information can be generated and provided to the surgeon to assist in guiding the surgeon to a lesion within the patient. For example, the orientation information can assist the surgeon in determining if an incision instrument is aligned with a particular axis of the marker and/or a boundary of the lesion.

At operation 714, a distance to the lesion and/or the identified marker is determined. For instance, the distance may be determined by at least one processor, such as processor 152 in operating environment 150 discussed above. The determination may be based on the identification of the marker and the data available from the detected reflected ultrasonic sound waves. The determined distance may be at least one of a distance from a portion of the ultrasound probe to the at least one of the marker or the lesion, a distance from a portion of a scalpel to the at least one of the marker or the lesion, or a distance from a portion, such as the tip, of an incision instrument to the at least one of the marker or the lesion. In determining the distance from the ultrasound probe to the marker, a calculation is performed based on the speed of sound based on the tissues through which the ultrasonic sound waves passed. For example, the speed of sound is known for the various tissues in the human body, and a distance calculation can be performed based on the travel time of the ultrasonic sound waves. Identification of the orientation of various devices in the ultrasound localization system also allows for the location to be determined in three-dimensional space and the determined distance may include a directional component, such as a vector.

Figure 7B:
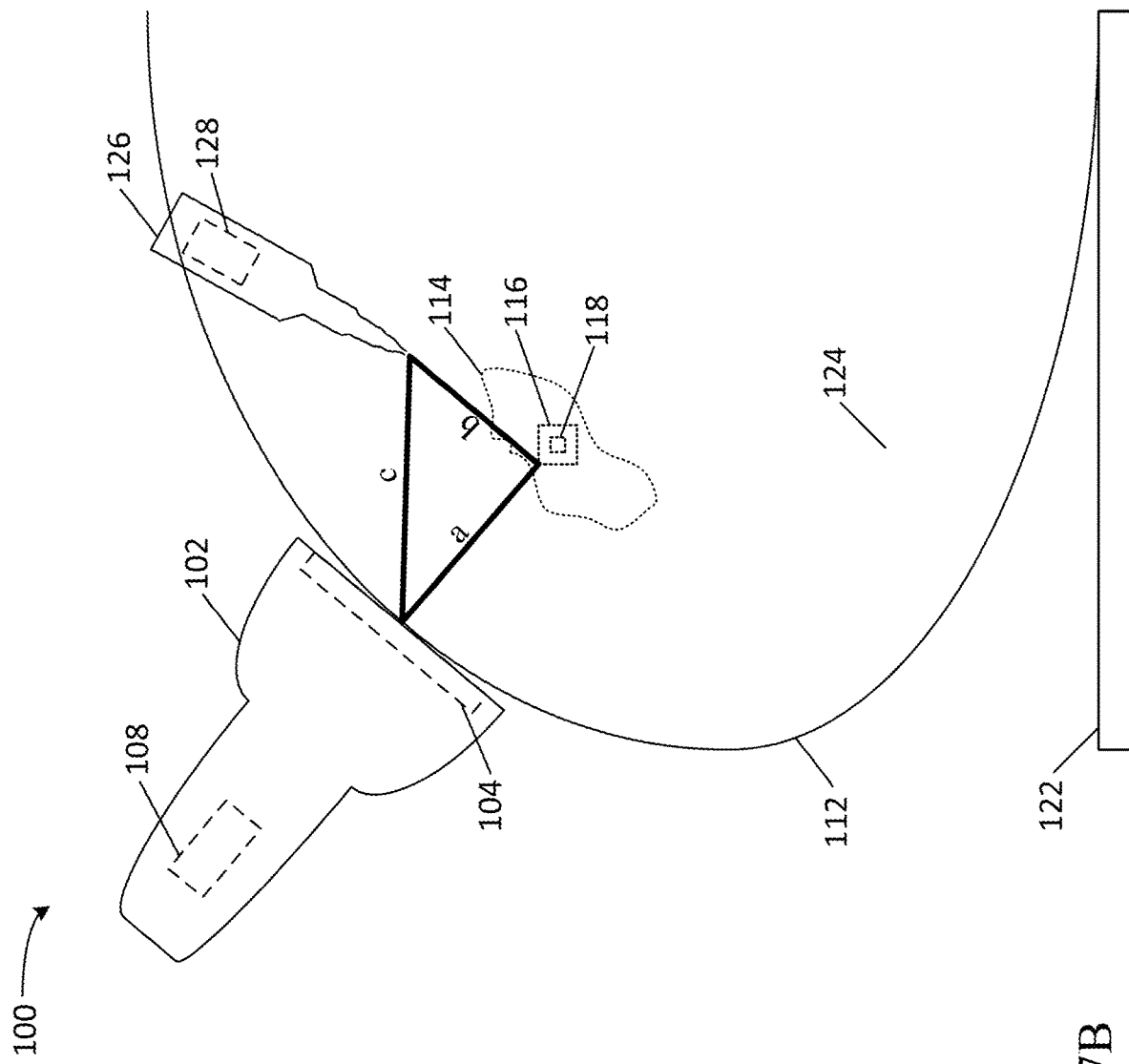
FIG. 7B depicts an example of ultrasound imaging including a method of calculating distance from incision instrument to the marker.

In some examples, a portion of the incision instrument, such as the tip of the incision instrument, can be identified in the ultrasound image data. The distance to the incision instrument from the ultrasound probe can be determined from the detected reflected ultrasonic sound waves in a similar manner as determining the distance to the marker. Based on the distance from the ultrasound probe to the marker and the distance from the ultrasound probe to the incision instrument, a distance from the marker to the incision instrument may also be determined. In some examples, the determination can be made using trigonometry principals such as laws of cosines. One example of the method of determining the distance to the marker is shown in FIG. 7B. In the figure, the distance from the ultrasound probe 102 to the marker 116 is shown as "a," the distance between the marker 116 and the incision instrument 126 is shown as "b", and the distance from the ultrasound probe 102 to the incision instrument 126 is shown as distance "c." The relationships between the distances may be represented as $a^2+b^2=c^2$. Accordingly, with two of the distances being determined from ultrasound depth calculations and/or lateral distance measurements from an ultrasound image, the other distance may be determined. Similarly, where one of the distances and one or more internal angles are determined, the other distances may also be determined through the use of trigonometric principles.

Determining the distance to the edge of a lesion may be based on the distance to the marker as well as the orientation of the marker. As discussed above, the orientation of the marker may be determined from the cross-section of the marker. For example, at the time the marker is inserted into the patient, the relative size and shape of the lesion may also be determined through various imaging techniques, including ultrasound, mammography, tomography, etc. When the marker is inserted, a representation of the edge of the lesion may be generated relative to the location and orientation of the marker. For instance, the edge of the lesion may be represented as a function of the location and orientation of the marker. Thus, when the distance and orientation of the marker are determined, the distance to the edge of a lesion may also be determined.

Once the distance to the lesion or the marker is determined by the processor of the ultrasound localization system, at operation 716, the determined distance is displayed on the display the operatively connected to the processor. For example, the distance may be displayed in a user interface element on the display. Other techniques for displaying or otherwise providing an indication of the determined distance are also possible, such as a dedicated indicator or an audible indicator. In other examples, the distance may be displayed or indicated on the ultrasound probe or the incision instrument.

Distances to the lesion or marker may be determined from multiple orientations as well. Determining the distance to the lesion or marker in multiple orientations may further define the location of the marker or lesion in three-dimensional space. The ultrasound system can use software beam forming techniques to lock on to the shape of the marker based on the fact that the marker is the same shape from two separate positions, in examples where the marker has such a geometry. Other image analysis techniques as discussed above may be used to identify the marker and lock on to the marker during imaging.

Figure 8A:
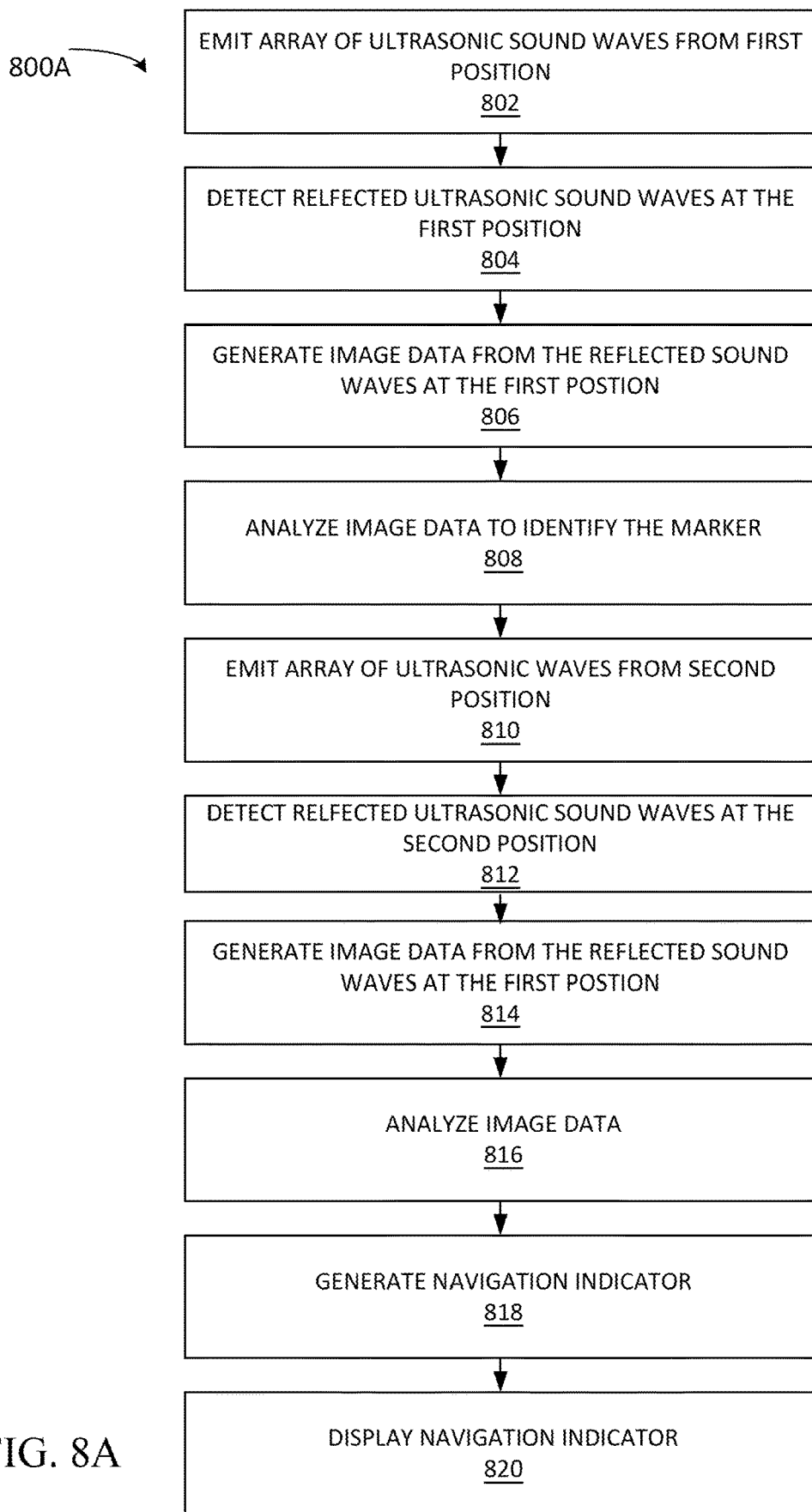
FIG. 8A depicts another example method for localization and navigation to an implanted marker.

FIG. 8A depicts an example method 800A for localization and navigation to an implanted marker. As detailed above, the marker may have been implanted at or near the lesion sometime prior to a surgical procedure. For instance, when the lesion was detected in a patent, the marker may have been implanted during a biopsy procedure. Thereafter, even months later, the marker may be used for localization during treatment or examination. In this way, rather than requiring coordination and placement of a localization wire at the time of surgery, the previously-implanted marker may be utilized to localize the lesion during the surgical procedure. Thus, logistics and scheduling on the day of surgery are simplified, as well as reducing an overall surgical time for the patient. Further benefits are realized because the implanted marker may be specially designed for detection using ultrasound or other imaging technologies to provide live imaging and lesion location data during the surgical procedure.

At operation 802, an array of ultrasonic sound waves are emitted from an ultrasonic transducer of an ultrasound probe at a first position. The ultrasound waves enter the interior of the patient and are reflected from the components of the interior of the patient, including natural tissue as well as the implanted marker, as discussed above. The reflected ultrasonic waves are then detected at the first position, at operation 804. At operation 806, ultrasound image data is then generated from the detected reflected ultrasonic sound waves at the first position of the ultrasound probe.

At operation 808, the image data is analyzed by a processor of the ultrasound localization system to identify or detect the implanted marker within the image data, using any of the techniques discussed above. In some examples, an ultrasound image may also be displayed showing the identified marker. In such examples, the marker may be highlighted or otherwise emphasized using any of the techniques described above.

Other indicators may also be triggered when the marker is identified and in the field of view. For instance, an audible sound, such as beep, may be emitted when the marker comes within a field view. In some examples, a tone having a varying frequency or intensity may also be emitted based on how close the marker is to the center of the field of view. Lights of other visual indicators may also be displayed when the marker comes into the field of view. Haptics on the ultrasound probe may also be activated when the marker comes into the field of view.

In some examples, signals from the various localization transceivers are processed by at least one of the processors in the ultrasound localization system to determine orientation and/or localization information for the ultrasound probe, the marker, and/or the incision instrument. Any of the techniques described above may be utilized for processing the signals and using the resultant information. For instance, a distance to the marker or the edge of the lesion may be determined and displayed, as discussed above.

In some cases, the ultrasound technician may move the ultrasound probe from the first position to a second position. The second position may differ from the first position in orientation of the ultrasound probe, location of the ultrasound probe, or both. With the ultrasound probe in the second position, at operation 810, an array of ultrasonic sound waves are emitted from the ultrasonic transducer of the ultrasound probe at a second position. The ultrasound waves enter the interior of the patient and are reflected from the components of the interior of the patient. The reflected ultrasonic waves are then detected at the second position, at operation 812. At operation 812, ultrasound image data is then generated from the detected reflected ultrasonic sound waves at the second position of the ultrasound probe.

At operation 814, the image data is analyzed by a processor of the ultrasound localization system to attempt to detect the implanted marker within the image data, using any of the techniques discussed above. At operation 814, however, the image analysis techniques fail to locate the marker within the image data from the second position because the marker is not within the field of the view of the ultrasound probe in the second position.

Based on the marker not being detected in operation 816, a navigation indicator is generated at operation 818. As discussed above, the navigation indicator provides navigation guidance for the ultrasound technician to find the marker. The navigation indicator may be based on the ultrasound identification of the marker when the ultrasound probe was in the first position. For example, the location and orientation of the ultrasound probe may be tracked or recorded from the first position to the second position. As such, providing guidance to return to a position where the marker can be seen and identified, e.g., a position where the marker is within the field of view, is possible. In other examples, the signals from the various localization transceivers may be used to determine the location of the marker and generate the navigation indicator. As discussed above, the ultrasound localization system may include at least a probe localization transceiver, a marker localization receiver, and/or an instrument localization transceiver. Those transceivers emit signals providing localization information for the device to which they are attached or incorporated, e.g., the ultrasound probe, the marker, and/or the incision instrument. The signal(s) emitted by the transceiver(s) may be processed to determine the orientation or location of the ultrasound probe, the marker, and/or the incision instrument. The orientation and location of those devices be determined or provided relative to other items, such as the incision instrument, the marker, the ultrasound probe, a magnetic direction, a normal to gravity, etc. With the orientation and location of the devices, additional information can be generated and provided to the surgeon to assist in guiding the surgeon to a lesion within the patient. For example, when the orientation and location information of the ultrasound probe and the marker are known, directional information may be determined to position the ultrasound probe to bring the marker into the field of the view of the ultrasound probe.

At operation 820, the navigation indicator is displayed. Displaying the navigation indicator at operation 820 may include illuminating an indicator on a display or creating a graphical user interface element to direct the ultrasound technician to bring the marker into the field of view of the ultrasound probe. For instance, the navigation indicator may include a series of arrows. Individual arrows may be highlighted to direct the ultrasound technician to move the ultrasound probe in a particular direction, as described above. Other types of navigation indicators may also be utilized to provide guidance to the ultrasound technician to find the marker. For example, indicators may also be provided in the ultrasound probe itself to assist the technician in bring the marker into the field of view.

Figure 8B:
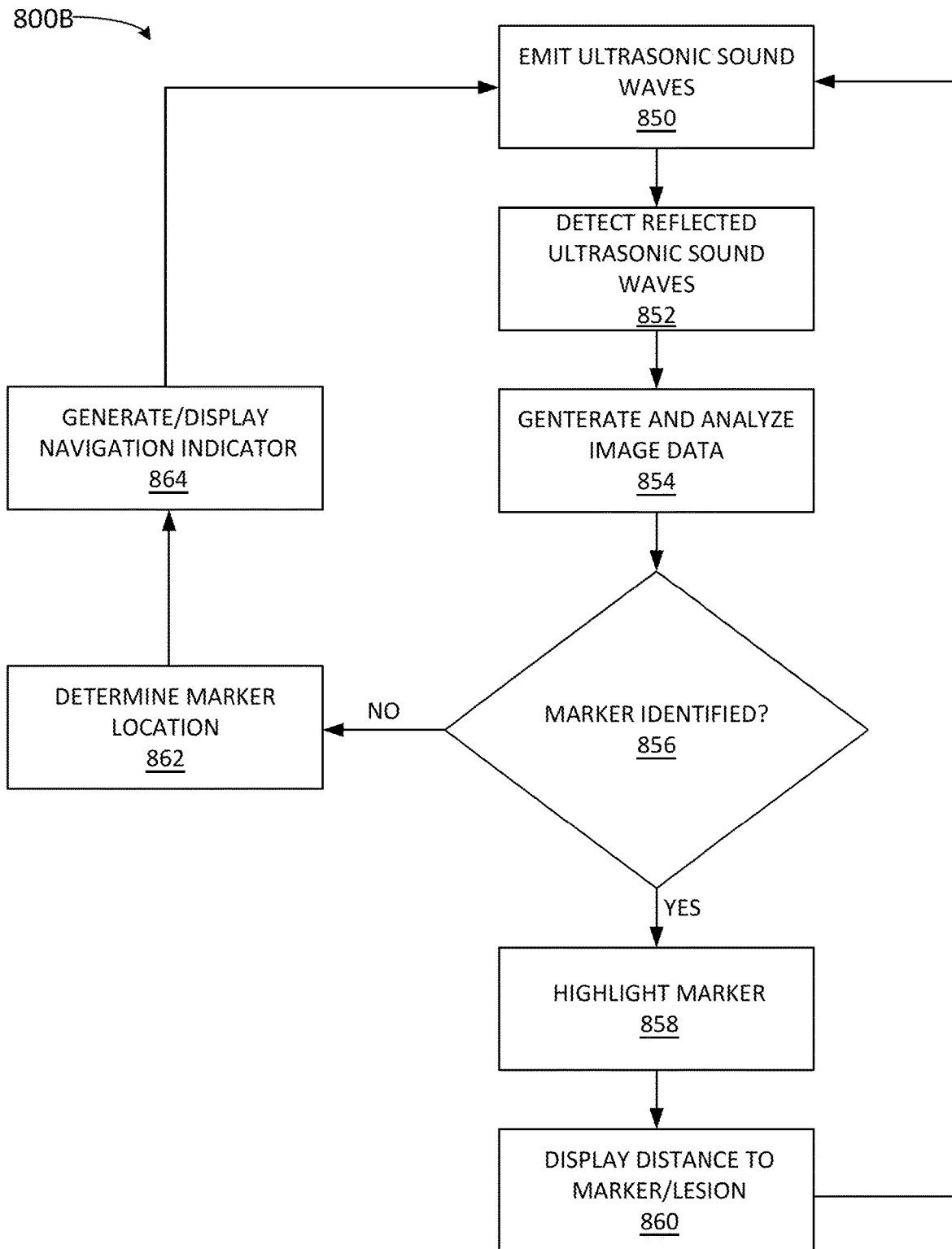
FIG. 8B depicts another example method for localization and navigation to an implanted marker.

FIG. 8B depicts another example method 800B for localization and navigation to an implanted marker. Method 800B provides for a continuous ultrasound imaging method that allows an ultrasound technician to continuously image a patient with the ultrasound probe and continue to receive feedback regarding the location of the marker and/or the lesion. At operation 850, an array of ultrasonic sound waves are emitted from an ultrasonic transducer of an ultrasound probe. The ultrasound waves enter the interior of the patient and are reflected from the components of the interior of the patient, as discussed above. The reflected ultrasonic waves are then detected at operation 852.

At operation 854, based on the reflected ultrasonic sound waves that are detected at operation 852, ultrasound image data is then generated and analyzed. Any of the image analysis techniques discussed above may be used. Based on the analysis of the image data at operation 854, a determination is made at operation 856 as to whether the marker has been identified or detected and is thus present in the ultrasound image data.

If the marker is determined to be present in the ultrasound image data at operation 856, the method 800B proceeds to operation 858 where the marker is highlighted or otherwise emphasized in an ultrasound image using any of the techniques described above. At operation 860, a distance to the marker and/or the lesion may also be determined and displayed using any of the techniques described above. The method 800B then flows back to operation 850 and method 800B repeats.

If the marker is determined not to be present in the ultrasound image data at operation 856, the method 800B proceeds to operation 862 where the marker location is determined. The location of the marker may be determined based on a prior identification of the marker in an ultrasound image and/or orientation and location information derived from signals from any of the localization transceivers, using any of the techniques described above. The determined location of the marker is then used to generate and display a navigation indicator at operation 864, using any of the techniques described above. From operation 864, the method 800B then flows back to operation 850 and method 800B repeats.

Figure 9:
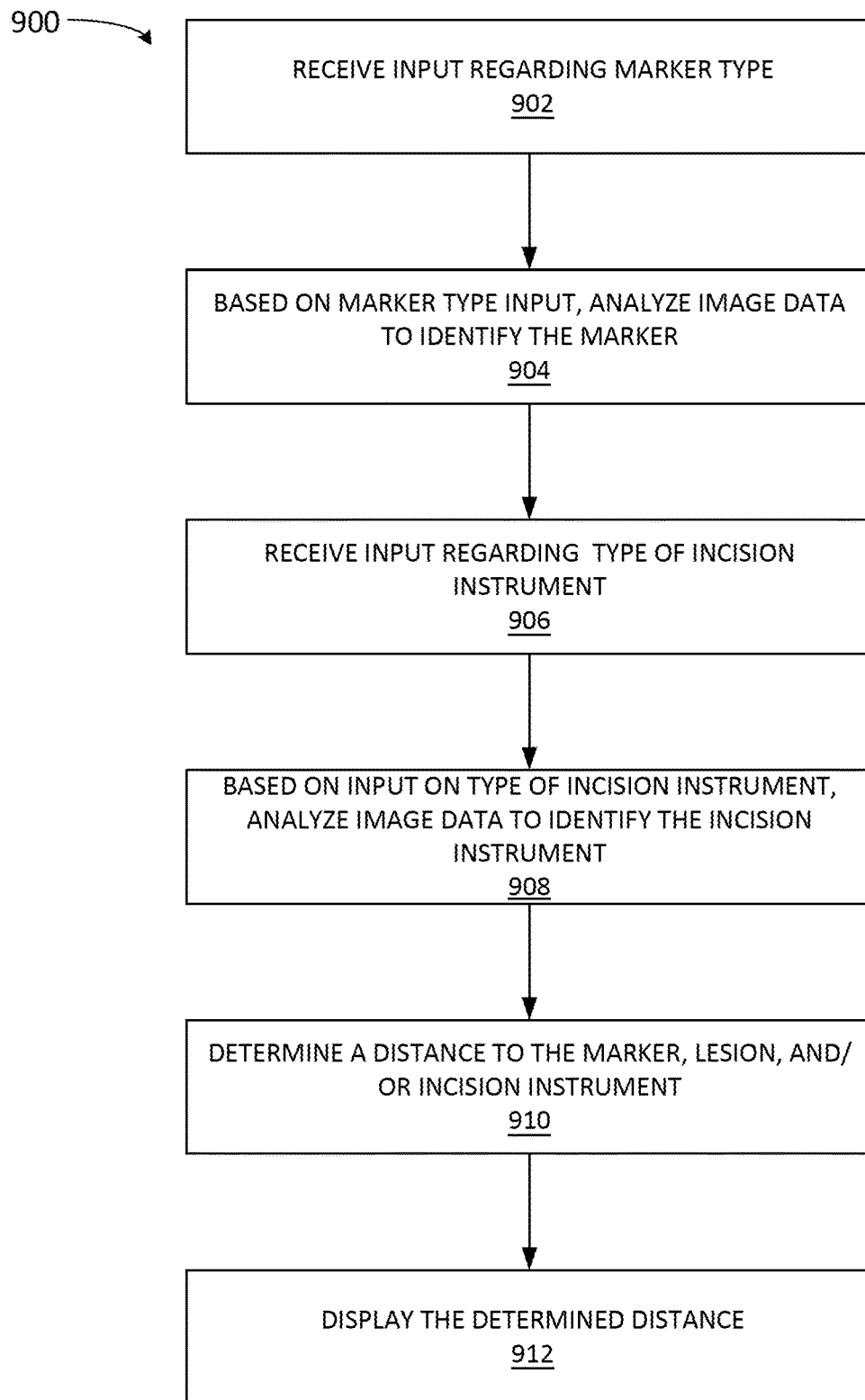
FIG. 9 depicts an example method for localization and detection of an implanted marker and an incision tool.

FIG. 9 depicts an example method 900 for localization and detection of an implanted marker and an incision tool. Method 900, or any subset of operations in method 900, may be used in combination and/or conjunction with any of the other methods discussed above. At operation 902, input regarding a type of marker is received from a user, such as an ultrasound technician. The input may be received from a user interface presented on the same display used for displaying the ultrasound image. For example, input may be provided indicating the type of marker that has been implanted in the patient. The input may indicate the shape and size of the marker. In an example, the input may include providing a model number or other identifying information for the marker. Based on the input, the dimensions and other information about the marker may be obtained, such as from a local or remote database storing such information. The dimensions of the marker may then be used by the image analysis techniques to assist in identification of the marker within the ultrasound image. At operation 904, based on the input regarding the marker type, the ultrasound image data is analyzed using image analysis techniques to identify the marker.

At operation 906, input regarding a type of incision tool is received from a user, such as an ultrasound technician. The input may be received from a user interface presented on the same display used for displaying the ultrasound image. The user interface may be the same user interface as the user interface used for gathering information on the type of marker. The input may be provided indicating the type of incision instrument that is being used with the patient. The input may indicate the shape and size of the incision tool or a portion of the incision tool. For example, the input may indicate the size and shape of the tip of a particular incision tool such as a scalpel. In an example, the input may include providing a model number or other identifying information for the incision instrument. Based on the input, the dimensions and other information about the incision instrument may be obtained, such as from a local or remote database storing such information. The dimensions of the incision instrument may then be used by the image analysis techniques to assist in identification of the incision instrument within the ultrasound image. At operation 906, based on the input regarding the incision instrument type, the ultrasound image data is analyzed using image analysis techniques to identify the incision instrument.

Once the marker and the incision instrument have been identified, a distance to the marker, the lesion, and/or the incision instrument may be determined at operation 910. The determined distance may be any of the determined distances discussed above and may utilize any of the techniques discussed above. As an example, the distance from the tip of the incision instrument to the marker may be determined from the ultrasound image. For instance, once the incision instrument is identified in the ultrasound image and the marker has been identified in the same image, the distance can be determined by measuring the distance between the two identified objects. The determination of the distance may be determined automatically by a processor in combination with the identification of the objects. The determination of the distance may also be done based on user input. For example, with the marker and incision instrument highlighted, or otherwise visually distinguished, on the ultrasound image, input can be provided to draw a line between the marker and the incision instrument. The length of the line may then be determined by the processor of the operating environment. Once the distance has been determined, the distance is displayed at operation 912.

Figure 10A:
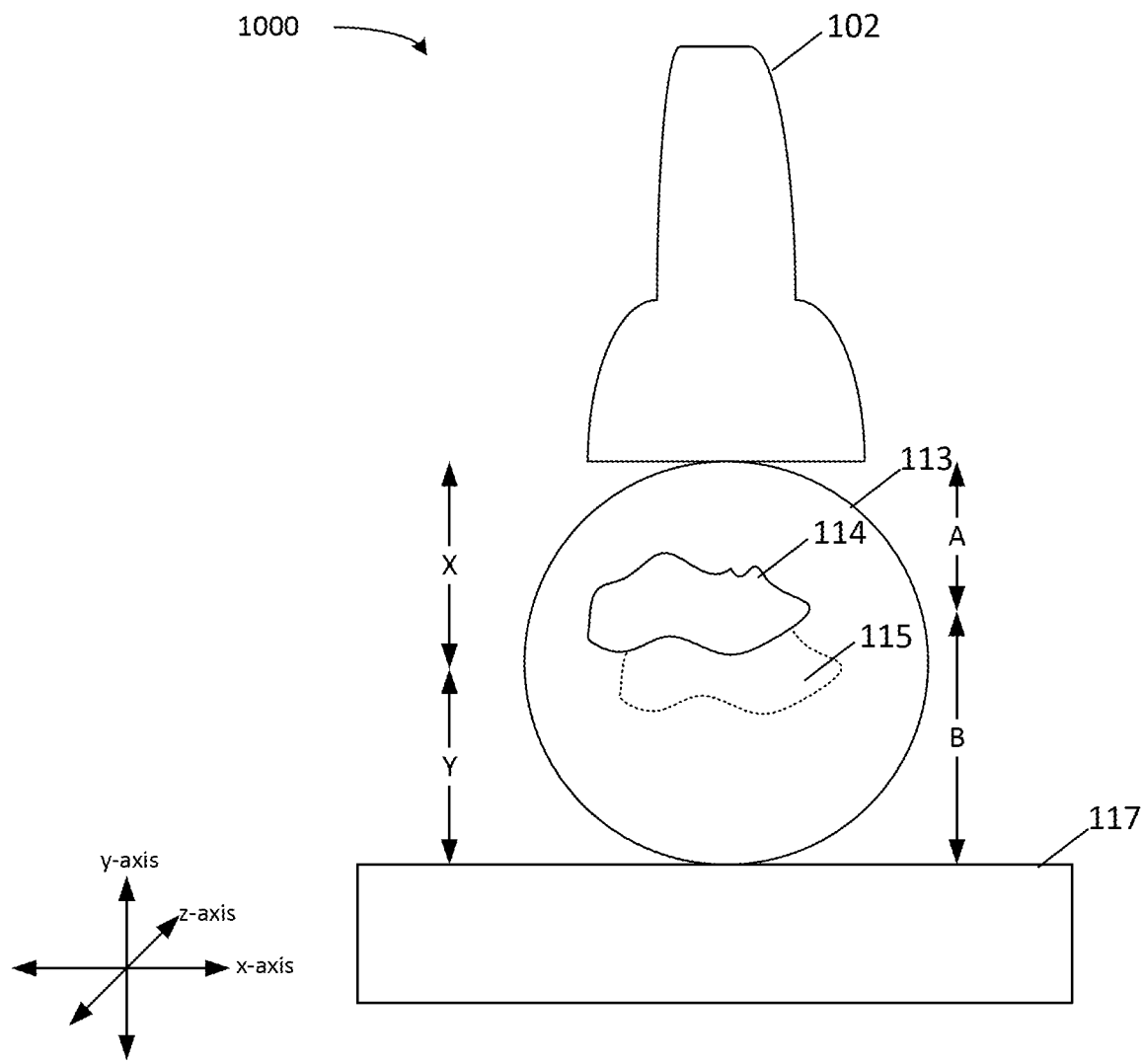
FIG. 10A depicts an example system for imaging a specimen.

FIG. 10A depicts an example system 1000 for imaging a specimen 117. Once a lesion 114 is removed during a surgical procedure, such as a lumpectomy, a surgeon may image the specimen 113 containing the lesion 114 to confirm that the margin of healthy tissue surrounds the lesion 114. Such an analysis of the margins helps ensure that all the abnormal tissue, such as cancerous tissue, has been removed from the region of interest of the patient. If the margins are not such that the surgeon feels confident that all the cancerous tissue has been removed, the surgeon returns to surgery to remove additional tissue. Current systems for imaging specimens, however, generally rely on x-ray exposures. These x-ray systems can take up significant space and are costly. The present technology provides an ultrasound-based solution that is able to both reduce the cost and footprint for imaging margins of a specimen removed from a patient during a surgical procedure. The use of the ultrasound technology allows for a quick imaging procedure and thus a quicker margin confirmation process. The ultrasound imaging procedure may also occur directly in the operating room. These benefits allow for shorter durations of surgeries.

To perform the imaging and margin confirmation, the specimen 113 is placed on a surface 117. An ultrasound probe 102 is placed on the specimen 113 to image the specimen 113. In the example illustrated, the specimen is spherically shaped for exemplary purposes. The theoretical, predicted, or ideal specimen location 115 (shown in dashed lines) is located at the center of the specimen 113. That predicted location 115 may be the location of where the surgeon believed the lesion 114 should be within the specimen. The predicted location 115 may be based on where the marker was located within the patient. In some examples, the marker is located in the specimen 113 at the location of the predicted location. The predicted location 115 is used for purposes of calculation to determine whether the margins of the specimen are sufficient. The distance to the predicted location 115 may be represented as a distance X from the top of the specimen to the center of the predicted location 115 and a distance Y from the center of the predicted location 115 to the surface 117. The distances X and Y represent the location of the predicted location 115. Where the predicted location 115 is in the center of the specimen 113, the distance X will be equal to distance Y.

The actual location of the lesion 114, however, may not be at the predicted location 115, as depicted in FIG. 10A. The ultrasound probe 102 is used to determine the actual location of the lesion 114 within the specimen 113. Through the distance measuring techniques of ultrasound technology discussed above, a distance A to the center of the lesion 114 from the ultrasound probe 102 and a distance B from the center of the lesion 114 to the surface 117 may be determined. In the example where the predicted location 115 was in the center of the specimen 113, if the difference between the distance A and the distance B is non-zero, the margin of the specimen 113 is not symmetric and the actual location of the lesion 114 is different from the predicted location 115. If the difference between the distance A and the distance B is greater than a predetermined threshold, the margins may be deemed insufficient and the surgeon may have to return to surgery to remove additional tissue. In addition, the difference between the distance A and the distance X may be determined, and if that difference exceeds a predetermined threshold, then the margins may be deemed insufficient. Similarly, the difference between the distance B and the distance Y may be determined, and if that difference exceeds a predetermined threshold, the margins may be deemed insufficient.

As a reference frame for the system 1000 depicted in FIG. 10A, the y-axis extends vertically through the image, the x-axis extends horizontally across the image, and the z-axis extends into the image. Accordingly, the distances X and Y and A and B are measured along the Y-axis in the example depicted in FIG. 10A.

Figure 10B:
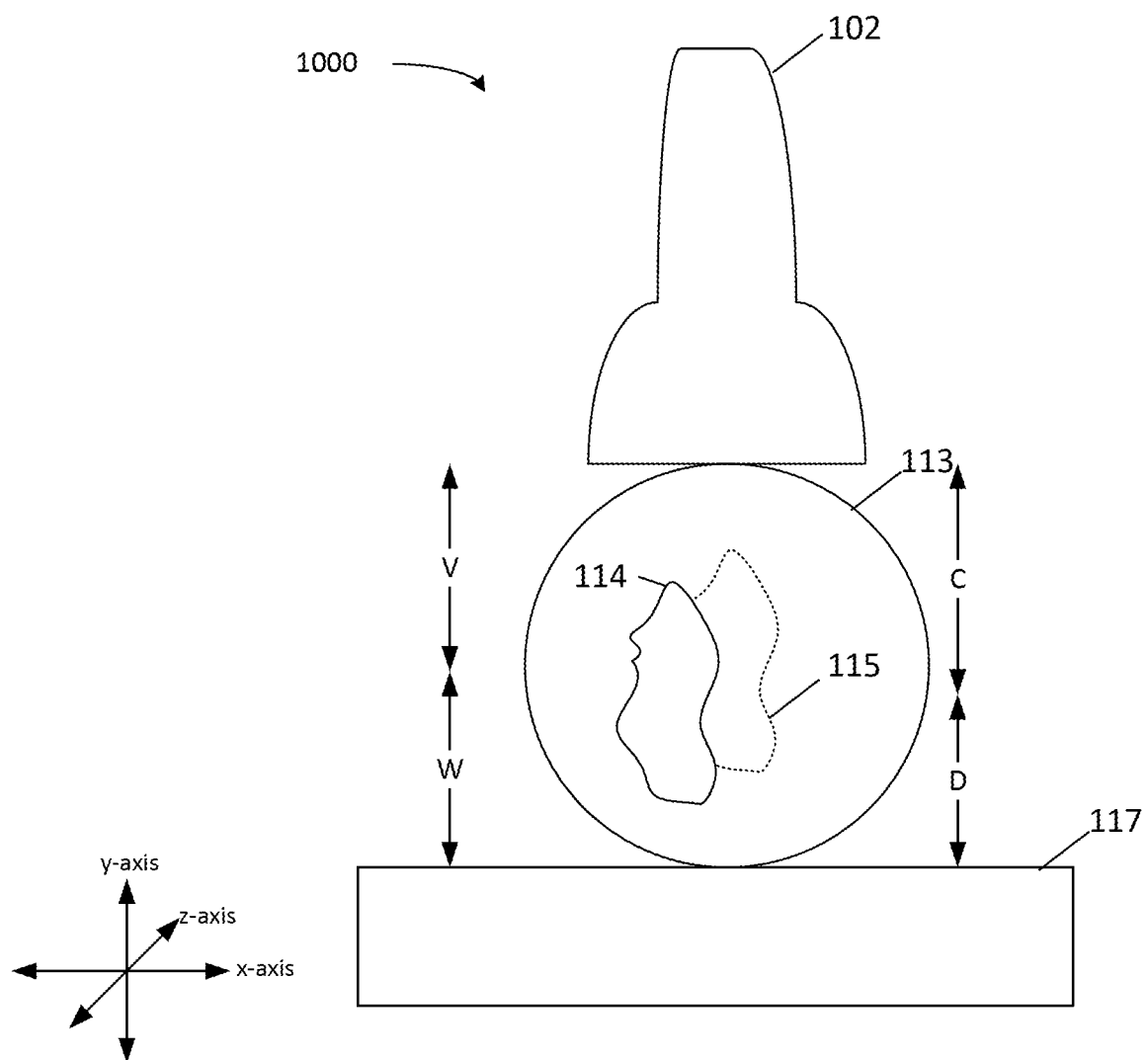
FIG. 10B depicts the ultrasound system of FIG. 10A with the specimen rotated.

To measure or determine additional margins from different orientations, the probe 102 or the specimen 113 may be rotated. FIG. 10B depicts the ultrasound system 1000 of FIG. 10A with the specimen rotated around the z-axis by 90 degrees. The distance to the center of the predicted location 115 from the probe 102 in this orientation is represented by the distance V and the distance from the center of the predicted location 115 to the edge of surface is represented by the distance W. Similar to the measurements in the prior orientation, margin verifications can be performed based on the differences between the respective distances. For instance, in the example where the predicted location 115 was in the center of the specimen 113, if the difference between the distance C and the distance D is non-zero, the margin of the specimen 113 is not symmetric and the actual location of the lesion 114 is different from the predicted location 115. If the difference between the distance C and the distance D is greater than a predetermined threshold, the margins may be deemed insufficient and the surgeon may have to return to surgery to remove additional tissue. In addition, the difference between the distance C and the distance V may be determined, and if that difference exceeds a predetermined threshold, then the margins may be deemed insufficient. Similarly, the difference between the distance D and the distance W may be determined, and if that difference exceeds a predetermined threshold, the margins may be deemed insufficient.

Figure 10C:
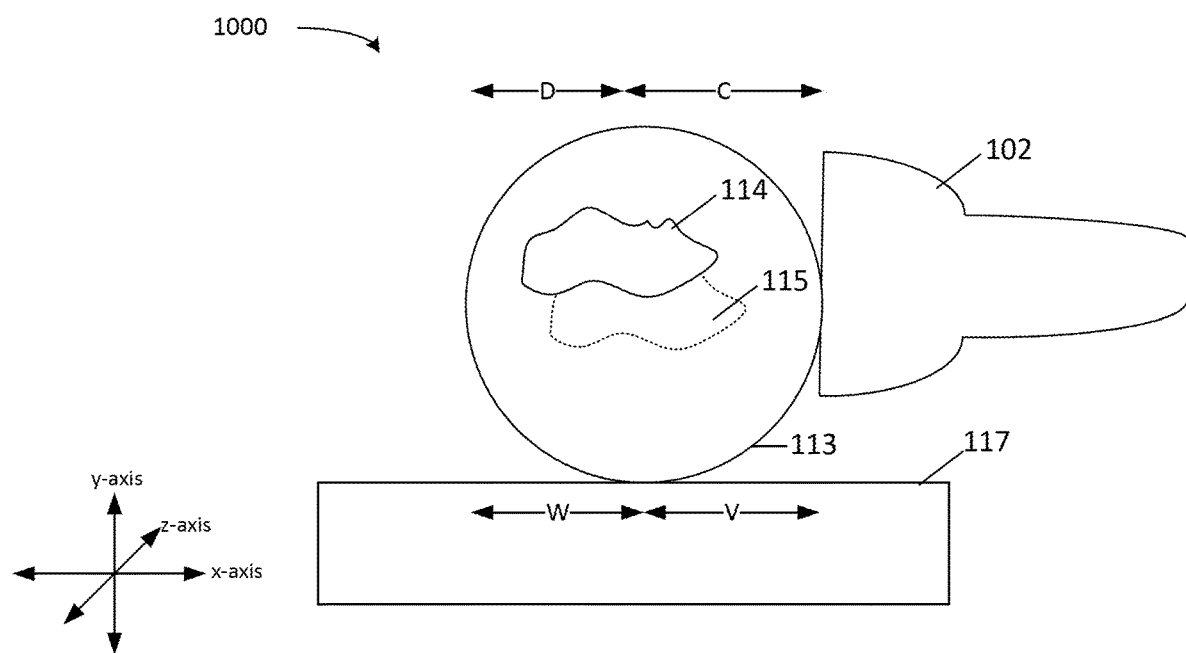
FIG. 10C depicts the ultrasound system of FIG. 10A with the ultrasound probe rotated.

FIG. 10C depicts the ultrasound system 1000 of FIG. 10A with the ultrasound probe rotated such that it oriented along the x-axis rather than the rotating the specimen. The same distances may be measured as were measured in the configuration of the specimen 113 and the probe 102 depicted in FIG. 10B. For instance, the distance to the center of the predicted location 115 from the probe 102 along the x-axis is represented by the distance V and the distance from the center of the predicted location 115 to the edge of the specimen 113 opposite the probe is represented by the distance W. In some implementations, rotating the specimen 113 may be favored over rotating the ultrasound probe 102 due the reflections of ultrasound waves off of the surface 117. Such reflections may make distance measurements from the probe to the edge of the specimen 113 on the surface 117 easier to determine.

While effectively only two different relative orientations have been depicted, the probe 102 or the specimen 113 may be rotated to measure from any additional orientations. For instance, the probe 102 may be rotated to be aligned with the z-axis, and measurements of the specimen 113 and lesion 114 may be measured along the z-axis. With the distances to the lesion measured along three planes, such as along the x-axis, y-axis, and z-axis, the location of the lesion in three-dimensional space can be determined. Thus, the margins of the lesion 114 within the specimen 113 may be determined.

In addition, distances from the exterior of the specimen 113 to the edge of the lesion 114 may be directly measured with use of the ultrasound probe 102. That is, the actual margin between the edge of the lesion 114 and the edge of the specimen 113 may be directly measured. The specimen 113 may be imaged at as many orientations as desired to determine whether the actual margins satisfy the desired or predetermined margins. For example, if a surgeon desires that the margins on all sides of the lesion 114 be greater than 5 millimeters, the ultrasound system 1000 may measure the margins to verify that such margins are present in the specimen 113. In some examples, the measurement and verification may be automated by the ultrasound system 1000. For example, as the ultrasound probe 102 moves around the specimen 113, measurements of the margins at each orientation may be measured. If at any point the margin is less than the desired, required, or predetermined margin (e.g., 5 mm), an alert or alarm may be generated. The alert along with the location and orientation of the probe relative to the specimen may be recorded and displayed or incorporated into a report. As such, a full scan of the specimen may be completed at each occurrence of a margin being less than the desired margin may be recorded and reported or displayed. The surgeon may then access the report or display to determine in which directions additional tissue needs to be removed from the patient.

It is also contemplated within the scope of this disclosure that the specimen is placed in a container and placed on a table. The geometries of the container are subtracted from the specimen geometries and the depth of the marker is calculated. It is also contemplated within the scope of the disclosure that the calculations shown above can apply to other geometries of the specimen. The specimen can be any shape and more complex calculations can be performed to determine the distances to the center of the marker or lesion and the specimen. The different shapes of the specimen can be stored in the ultrasound system and automatically matched to a particular profile to help facilitate the calculations and margin determinations.

Figure 11:
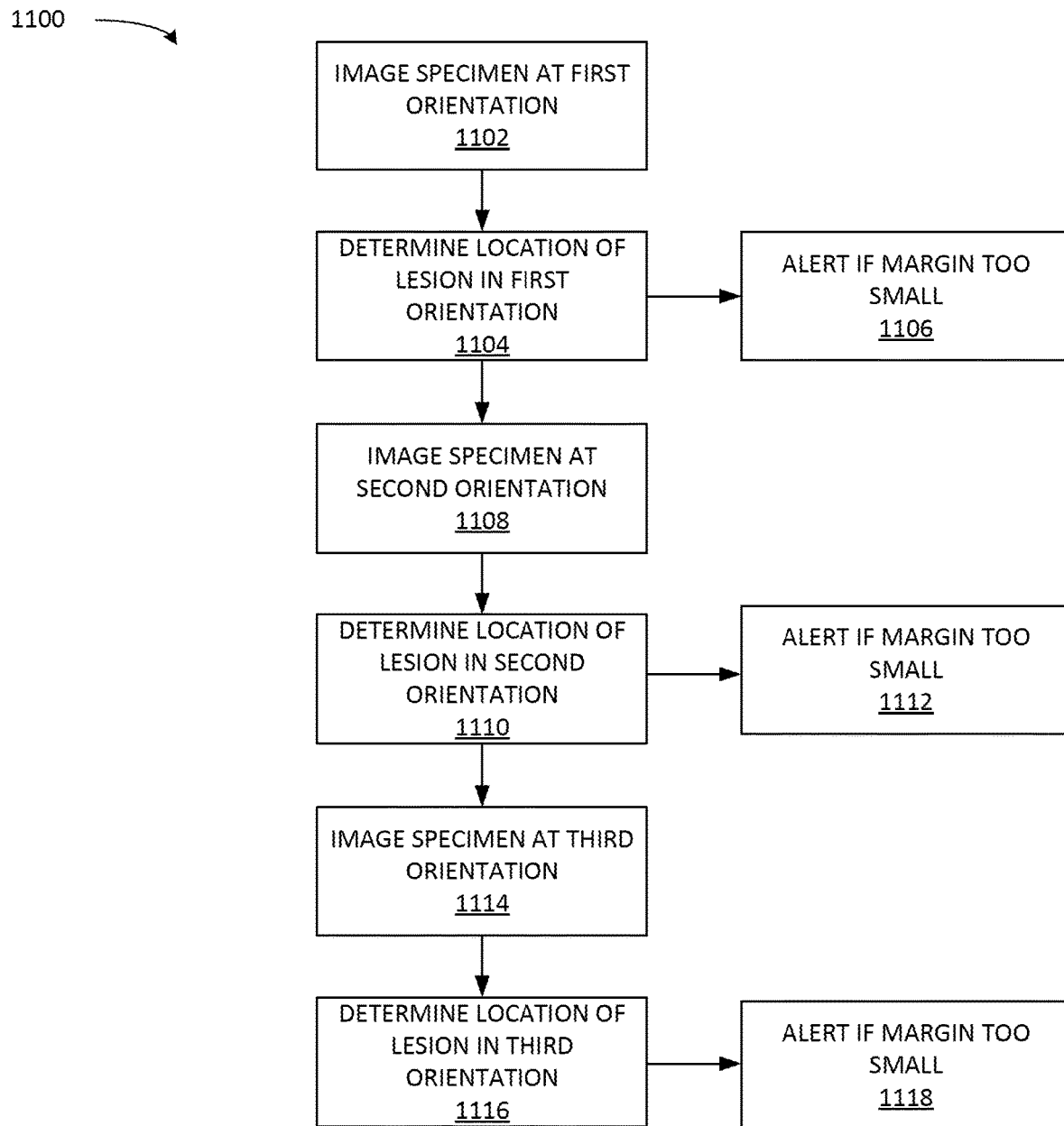
FIG. 11 depicts a method for confirming margins of a specimen.
Figure 12C:
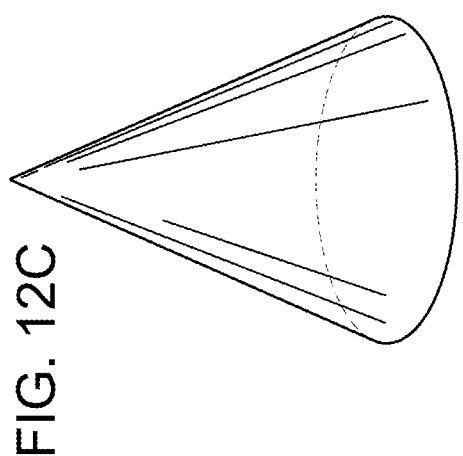
FIGS. 12A-12F depict examples of implanted markers.
Figure 12B:
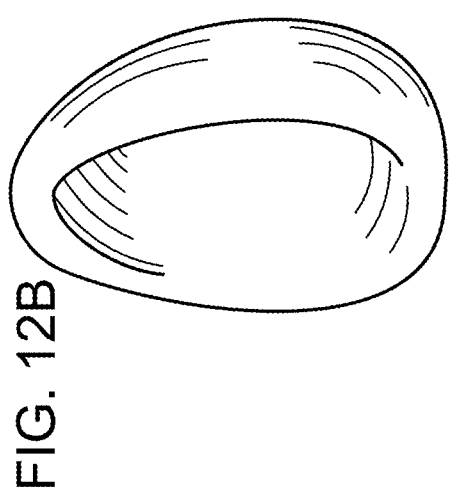
Figure 12A:
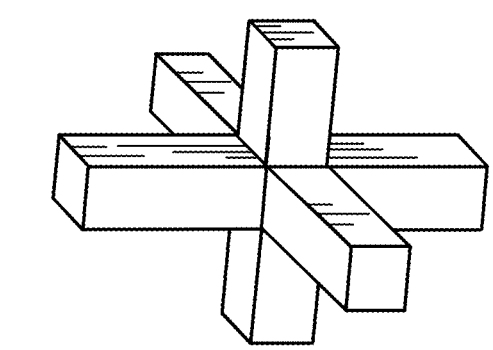
Figure 12F:
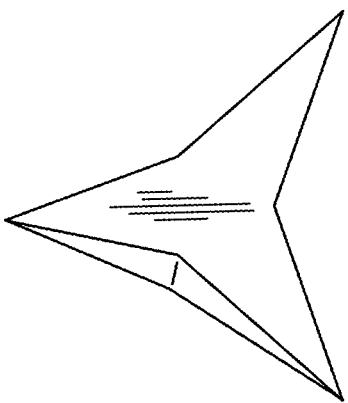
Figure 12E:
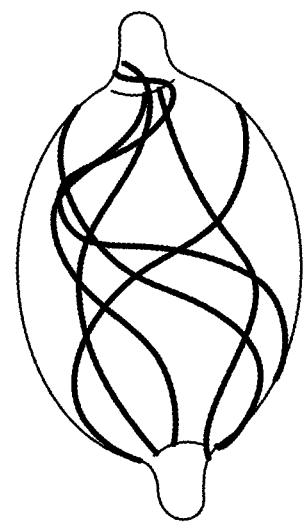
Figure 12D:
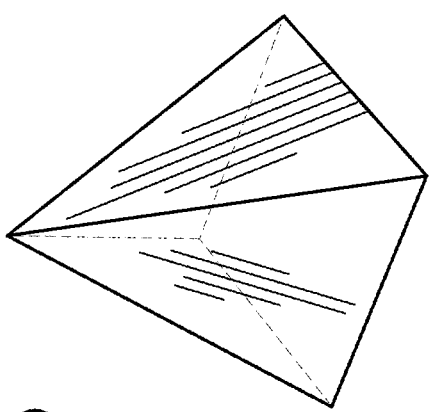

FIG. 11 depicts a method 1100 for confirming margins of a specimen. At operation 1102, a specimen containing a lesion is imaged in a first orientation using an ultrasound probe. The first orientation may be along a particular axis, such as the y-axis. Imaging the specimen may include emitting an array of ultrasonic sound waves from an ultrasonic transducer of the ultrasound probe. The ultrasound waves enter the interior of the specimen and are reflected from the components of the interior of the specimen, similar to how the ultrasonic sound waves interact with the interior of the patient as discussed above. The reflected ultrasonic waves are then detected, and based on the reflected ultrasonic sound waves ultrasound image data is then generated that can be analyzed. At operation 1104, based on the imaging of the lesion at operation 1102, the location of the lesion in the first orientation may be determined. Determining the location of the lesion may include determining distances to the center of the lesion from the probe and/or the distance from the center of the lesion to the surface, such as distance A and distance B discussed above with reference to FIG. 10A. Determining the location of the lesion may also include determining whether one or more margins in the first orientation are within an acceptable range or greater than the desired margins of the surgeon. Such a determination may be made by a direct measurement of distance from the probe to the edge of the lesion and then comparing that measurement to the desired margin. The determination may also be determined by comparing the location of the lesion in the first orientation with a predicted location of a lesion, as discussed above with reference to FIG. 10A. If the determined margins of the specimen are below the desired margins, an alert may be generated at operation 1106. The alert may be audible or visual. For instance, an alert indicating the margin at the current orientation is too small. The alert may also be recorded or otherwise reported to the surgeon along with details of the current orientation so that the surgeon is able to determine where additional tissue needs to be removed from the patient.

At operation 1108, the specimen is imaged at a second orientation, such as along the x-axis. Imaging the specimen at the second orientation may involve rotating the specimen to the second orientation or rotating the probe to the second orientation. At operation 1110, based on the imaging of the lesion at operation 1108, the location of the lesion in the second orientation may be determined. Determining the location of the lesion may include determining distances to the center of the lesion from the probe and/or the distance from the center of the lesion to the surface, such as distance C and distance D discussed above with reference to FIGS. 10B-10C. Determining the location of the lesion may also include determining whether one or more margins in the first orientation are within an acceptable range or greater than the desired margins of the surgeon. Such a determination may be made by a direct measurement of distance from the probe to the edge of the lesion and then comparing that measurement to the desired margin. The determination may also be determined by comparing the location of the lesion in the second orientation with a predicted location of a lesion, as discussed above with reference to FIG. 10B. If the determined margins of the specimen are below the desired margins, an alert may be generated at operation 1112. The alert may be substantially the same as the alert generated in operation 1106 but for the second orientation.

At operation 1114, the specimen is imaged at a third orientation, such as along the z-axis. Imaging the specimen at the third orientation may involve rotating the specimen to the third orientation or rotating the probe to the third orientation. At operation 1116, based on the imaging of the lesion at operation 1114, the location of the lesion in the third orientation may be determined. Determining the location of the lesion and the margins for the specimen may be similar to the techniques discussed above, but for the third orientation. If the determined margins of the specimen are below the desired margins, an alert may be generated at operation 1118. The alert may be substantially the same as the alert generated in operations 1106 and 1112 but for the second orientation. Method 1000 may then repeat for additional orientations beyond the first three orientations. For instance, the specimen may be continuously imaged at a variety of angles or orientations. At each orientation, a margin determination may be made and reported.

As should be appreciated, the operations described in the above methods are described for purposes of illustrating the present methods and systems and are not intended to limit the disclosure to a particular sequence of steps, e.g., steps may be performed in differing order, additional steps may be performed, and disclosed steps may be excluded without departing from the present disclosure.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A method for localization of an implanted marker with ultrasound technology, the method comprising:
   providing a marker implanted proximate a lesion within an interior of a patient, the marker having a marker localization transceiver and at least one detector;
   emitting ultrasonic sound waves from an ultrasonic transducer of an ultrasound probe;
   detecting reflected ultrasonic sound waves by the ultrasonic transducer, wherein the reflected ultrasonic sound waves include at least a portion of the emitted ultrasonic sound waves after being reflected from the marker;
   generating an image from image data from the reflected ultrasonic sound waves;
   receiving a signal containing marker data and lesion data from the marker localization transceiver;
   processing, by a processor, the signal received from the marker localization transceiver to determine (1) a location of the marker based on the marker data, and (2) changes regarding the lesion based on the lesion data;
   displaying, on a display operatively connected to the processor, the image with (1) the location of the marker, and (2) the changes regarding the lesion; and
   based at least in part on the location of the marker, emitting an audible sound, wherein the audible sound is based on how close the marker is to a center of a field of view of the image displayed on the display.

2. The method of claim 1, further comprising based on the location of the marker, determining, by the processor, a distance to at least one of the marker or the lesion.

3. The method of claim 2, wherein the distance to the at least one of the marker or the lesion is based on at least one of a location of the ultrasound probe or an orientation of the ultrasound probe.

4. The method of claim 3, further comprising:
   receiving a signal from a probe localization transceiver, wherein the probe localization transceiver is attached to the ultrasound probe; and
   processing, by the processor, the signal received from the probe localization transceiver to determine the at least one of the location of the ultrasound probe or the orientation of the ultrasound probe.

5. The method of claim 2, wherein the distance to the at least one of the marker or the lesion is based on at least one of a location of an incision instrument or an orientation of the incision instrument.

6. The method of claim 5, further comprising:
   receiving a signal from an instrument localization transceiver, wherein the instrument localization transceiver is attached to the incision instrument; and
   processing, by the processor, the signal received from the instrument localization transceiver to determine the at least one of the location of the incision instrument or the orientation of the incision instrument.

7. The method of claim 1, wherein the marker includes a receiver configured to convert wave energy into electrical energy, and the method further comprises controlling the marker localization transceiver to send the signal based on wave energy.

8. The method of claim 7, further comprising activating the marker localization transceiver by the emitted ultrasonic sound waves.

9. The method of claim 7, further comprising powering the marker localization transceiver with an inductive power supply configured to generate an electromagnetic wave.

10. The method of claim 1, wherein the signal from the marker localization transceiver includes a unique identifier, the method further comprising displaying the unique identifier on the display.

11. The method of claim 1, wherein the signal from the marker localization transceiver is a radio frequency identification signal.

12. A system for ultrasound localization, the system comprising:
   a marker comprising a marker localization transceiver configured to emit a signal containing marker data and lesion data, and at least one detector, wherein the marker is configured to be implanted proximate a lesion within an interior of a patient;
   an ultrasound probe comprising an ultrasonic transducer, the ultrasonic transducer configured to emit ultrasonic sound waves and detect reflected ultrasonic sound waves, wherein the reflected ultrasonic sound waves include at least a portion of the emitted ultrasonic sound waves after being reflected from the marker;
a display;
at least one processor operatively connected to the marker, the ultrasound probe, and the display; and
memory, operatively connected to the at least one processor, storing instructions that when executed by the at least one processor perform a set of operations comprising:
generating an image from image data from the reflected ultrasonic sound waves;
receiving a signal containing marker data and lesion data from the marker localization transceiver;
processing the signal received from the marker localization transceiver to determine (1) a location of the marker based on the marker data, and (2) changes regarding the lesion based on the lesion data;
displaying on the display the image with (1) the location of the marker, and (2) the changes regarding the lesion; and
based at least in part on the location of the marker, emitting an audible sound, wherein the audible sound is based on how close the marker is to a center of a field of view of the image displayed on the display.

13. The system of claim 12, wherein the set of operations that the at least one processor performs further comprises based at least in part on the location of the marker, determining, a distance to at least one of the marker or the lesion.

14. The system of claim 13, wherein the distance to the at least one of the marker or the lesion is based on at least one of a location of the ultrasound probe or an orientation of the ultrasound probe.

15. The system of claim 14, wherein the ultrasound probe further comprises a probe localization transceiver, wherein the probe localization transceiver transmits data to indicate the at least one of the location of the ultrasound probe or the orientation of the ultrasound probe.

16. The system of claim 13, further comprising an incision instrument, wherein the distance to the at least one of the marker or the lesion is based on at least one of a location of the incision instrument or an orientation of the incision instrument.

17. The system of claim 16, wherein the incision instrument comprises an instrument localization transceiver, wherein the instrument localization transceiver transmits data to indicate the at least one of the location of the incision instrument or the orientation of the incision instrument.

18. The system of claim 12, wherein the marker includes a receiver configured to convert wave energy into electrical energy, and the marker localization transceiver is controllable to send the signal based on wave energy.

19. The system of claim 18, wherein the marker localization transceiver is configured to be activated by the emitted ultrasonic sound waves.

20. The system of claim 18, further comprising an inductive power supply configured to generate an electromagnetic wave and power the marker localization transceiver.

21. The system of claim 12, wherein the signal from the marker localization transceiver includes a unique identifier, and the unique identifier is displayed on the display.

22. The system of claim 12, wherein the signal from the marker localization transceiver is a radio frequency identification signal.

* * * * *